US011763451B2

(12) United States Patent
Mattrey et al.

(10) Patent No.: US 11,763,451 B2
(45) Date of Patent: *Sep. 19, 2023

(54) MICROBUBBLE AND NANOBUBBLE EXPANSION USING PERFLUOROCARBON NANODROPLETS FOR ENHANCED ULTRASOUND IMAGING AND THERAPY

(71) Applicant: The Board of Regents of The University of Texas System, Austin, TX (US)

(72) Inventors: Robert F. Mattrey, Dallas, TX (US); Caroline De Gracia Lux, Dallas, TX (US); Jacques Lux, Dallas, TX (US); Zhenghong Gao, Dallas, TX (US); Carlos J. Brambila, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,423

(22) Filed: May 13, 2022

(65) Prior Publication Data
US 2023/0005134 A1   Jan. 5, 2023

Related U.S. Application Data

(63) Continuation of application No. 16/798,876, filed on Feb. 24, 2020, now Pat. No. 11,334,993.
(Continued)

(51) Int. Cl.
*G06T 7/00* (2017.01)
*G06T 7/62* (2017.01)
(Continued)

(52) U.S. Cl.
CPC .............. *G06T 7/0012* (2013.01); *A61N 7/02* (2013.01); *G06T 7/62* (2017.01);
(Continued)

(58) Field of Classification Search
CPC .................... G06T 7/0012; G06T 7/62; G06T 2207/10132; G06T 2207/20104;
(Continued)

(56) References Cited

U.S. PATENT DOCUMENTS 10,322,178 B2   6/2019   Chen et al.
2013/0336891 A1*  12/2013   Dayton .............. A61K 49/0002
424/490
(Continued)

FOREIGN PATENT DOCUMENTS

WO   WO 2009/052057   4/2009

OTHER PUBLICATIONS

Al-Husein et al., "Anti-angiogenic therapy for cancer: An update," Pharmacotherapy, Dec. 2012, 32(12):1095-1111.
(Continued)

*Primary Examiner* — Siamak Harandi
(74) *Attorney, Agent, or Firm* — Womble Bond Dickinson (US) LLP

(57) ABSTRACT

The disclosure describes imaging and therapy techniques comprising nanodroplets. More particularly, aspects of the disclosure relate to the use of nanodroplets to modify nanobubbles or microbubbles to provide improved imaging and/or therapeutic techniques and compositions.

20 Claims, 19 Drawing Sheets
(8 of 19 Drawing Sheet(s) Filed in Color)

Related U.S. Application Data

(60) Provisional application No. 62/809,280, filed on Feb. 22, 2019.

(51) Int. Cl.
*A61N 7/02* (2006.01)
*A61N 7/00* (2006.01)

(52) U.S. Cl.
CPC ............. *A61N 2007/0004* (2013.01); *A61N 2007/0039* (2013.01); *G06T 2207/10132* (2013.01); *G06T 2207/20104* (2013.01); *G06T 2207/30096* (2013.01)

(58) Field of Classification Search
CPC ............ G06T 2207/30096; A61N 7/02; A61N 2007/0004; A61N 2007/0039; A61N 7/00; A61B 8/481
See application file for complete search history.

(56) References Cited

U.S. PATENT DOCUMENTS

| | | |
|---|---|---|
| 2014/0243664 A1 | 8/2014 | El-Sayed et al. |
| 2016/0167061 A1 | 6/2016 | McNaughton et al. |
| 2017/0176305 A1 | 6/2017 | Shi et al. |
| 2018/0272012 A1 | 9/2018 | De Gracia Lux et al. |
| 2020/0320689 A1 | 10/2020 | Mattrey et al. |

OTHER PUBLICATIONS

Baskin et al., "Copper-free click chemistry for dynamic in vivo imaging," PNAS, Oct. 23, 2007, 104(43):16793-16797.
Behan et al., "Perfluorooctylbromide as a Contrast Agent for CT and Sonography: Preliminary Clinical Results," AJR, 1993, 160:399-405.
Beppu et al., "Prolonged myocardial contrast echocardiography via peripheral venous administration of QW3600 injection (EchoGen): its efficacy and side effects," J Am Soc Echocardiogr, Jan.-Feb. 1997, 10(1):11-24.
Borden et al., "Dissolution Behavior of Lipid Monolayer-Coated, Air-Filled Microbubbles: Effect of Lipid Hydrophobic Chain Length," Langmuir, 2002, 18(24):9225-9233.
Brudno et al., "In Vivo Targeting through Click Chemistry," ChemMedChem, Apr. 2015, 10(4):617-620, PMID: 25704998.
Caruso et al., "Heterogeneous delayed enhancement of hepatic parenchyma after intravenous infusion of sonographic contrast agent: a new hypothesis," Radiol Med, Feb. 2007, 112(1):56-63.
Chang et al., "Copper-free click chemistry for dynamic in vivo imaging," PNAS, Oct. 23, 2007, 104(43):16793-16797.
Chen et al., "Targeted Drug Delivery with Focused Ultrasound-Induced Blood-Brain Barrier Opening Using Acoustically-Activated Nanodroplets," J Control Release, 2013, 172(3):795-804.
Chomas et al., "Optical observation of contrast agent destruction," Appl Phys Lett, 2000, 77:1056-1058.
Cui et al., "Neutral progenitor cells labeling with microbubble contrast agent for ultrasound imaging in vivo," Biomaterials, Jul. 2013, 34(21):4926-4935.
Dayton et al., "The magnitude of radiation force on ultrasound contrast agents," J Acoust Soc Am, Nov. 2002, 112(5 Pt 1):2183-2192.
De Gracia Lux et al., "Novel method for the formation of monodisperse superheated perfluorocarbon nanodroplets as activatable ultrasound contrast agents," RSC Adv, 2017, 7, 48561-48568.
Ellegala et al., "Imaging Tumor Angiogenesis With Contrast Ultrasound and Microbubbles Targeted to Alpha-v Beta-3," Circulation, Jul. 2003, 108(3):336-341.
Ferretti et al., "Tumor Interstitial Fluid Pressure as an Early-Response Marker for Anticancer Therapeutics," NeoPlasia, Sep. 2009, 11(9):874-881.
Fink et al., "Time-Reversal Acoustics in Biomedical Engineering," Annu Rev Biomed Eng, 2003, 5:465-497.
Giesecke et al., "Ultrasound-mediated cavitation thresholds of liquid perfluorocarbon droplets in vitro," Ultrasound Med Biol, 2003, 29:1359-1365.
Grayburn et al., "Peripheral Intravenous Myocardial Contrast Echocardiography Using a 2% Dodecafluoropentane Emulsion: Identification of Myocardial Risk Area and Infarct Size in the Canine Mode of Ischemia," J Am Cardiol, 1995, 26(5):1340-1347.
Hall et al., "Time evolution of enhanced ultrasonic reflection using a fibrin-targeted nanoparticulate contrast agent," J Acoust Soc Am, 2000, 108(6):3049-3057.
Hauff et al., "Molecular Targeting of Lymph Nodes with L-Selectin Ligand-specific US Contrast Agent: A Feasibility Study in Mice and Dogs," Radiology, 2004 in press [Epub ahead of print].
Ho et al., "Theranostic Performance of Acoustic Nanodroplet Vaporization-Generated Bubbles in Tumor Intertissue," Theranostics, 2017, 7(6):1477-1488.
Hutter et al., "Physiologically Based Pharmacokinetic Model for Fluorocarbon Elimination After the Administration of an Octafluoropropane-Albumin Microsphere Sonographic Contrast Agent," J Ultrasound Med, 1999, 18:1-11.
Jolesz, "MRI-Guided Focused Ultrasound Surgery," Annu Rev Med, 2009, 60:417-430.
Jolesz et al., "Magnetic resonance image-guided focused ultrasound surgery," Cancer J, 2002, 8(Suppl 1):S100-112 (abstract only).
Jordan et al., "Effects of Magnetic Fluid Hyperthermia (MFH) on C3H mammary carcinoma in vivo," Int J Hyperthermia, 1997, 13(6):587-605.
Jordan et al., "Presentation of a new magnetic field therapy system for the treatment of human solid tumors with magnetic fluid hyperthermia," J Magn and Magn Mater, 2001, 225:118-126.
Klibanov et al., "Detection of Individual Microbubbles of an Ultrasound Contrast Agent: Fundamental and Pulse Inversion Imaging," Acad Radiol, 2002, 9(Suppl 2):5279-5281.
Klibanov et al., "Detection of individual microbubbles of ultrasound contrast agents: imaging of free-floating and targeted bubbles," Invest Radiol, 2004, 39(3):187-195.
Kooiman et al., "DSPC or DPPC as main shell component influences ligand distribution and binding area of lipid-coated targeted microbubbles," Eur J Lipid Sci Tech, 2014, 116(9):1217-1227.
Kripfgans et al., "Acoustic droplet vaporization for therapeutic and diagnostic applications," Ultrasound Med Bio, 2000, 26(7):1177-1189.
Lanza et al., "In Vivo Molecular Imaging of Stretch-Induced Tissue Factor in Carotid Arteries with Ligand-Targeted Nanoparticles," J Am Soc Echocardiogr, Jun. 2000, 13(6):608-614.
Leong-Poi et al., "Noninvasive Assessment of Angiogenesis by Ultrasound and Microbubbles Targeted to Alpha(v)-Integrins," Circulation, 2003, 107(3):455-460.
Lindner et al., "Ultrasound Assessment of Inflammation and Renal Tissue Injury With Microbubbles Targeted to P-Selection," Circulation, Oct. 23, 2001, 104(17):2107-2112.
Lo et al., "Acoustic droplet vaporization threshold: effects of pulse duration and contrast agent," IEEE Trans Ultrason Forroelectr Freq Control, 2007, 54(5):933-946.
Lux et al., "Thrombin-Activatable Microbubbles as Potential Ultrasound Contrast Agents for the Detection of Acute Thrombosis," ACS Appl Mater Interface, Nov. 1, 2017, 9(43):37587-37596.
Matsuoka et al., "Hyperthermia using magnetite cationic liposomes for hamster osteosarcoma," BioMag Res Technol, 2004, 2:3-8.
Mattrey, "Perfluorooctylbromide: A New Contrast Agent for CT, Sonography, and MR Imaging," AJR Am J Roentgenol, 1989, 152(2):247-252.
Mattrey et al., "Ultrasound Contrast Agents: State of the Art," Radio, 1991, 26:S5-S11.
Mattrey et al., "Perfluoroctyl bromide as a blood pool contrast agent for liver, spleen, and Vascular Imaging in Computed Tomography," J Comput Assist Tomogr, 1984, 8(4):739-744.
Miyoshi et al., "Detailed Analysis of the Surface Area and Elasticity in the Saturated 1,2-Diacylphosphatidylcholine/Cholesterol Binary Monolayer System," Langmuir, 2015, 31(33):9086-9096.
Moroz et al., "Magnetically mediated hyperthermia: current status and future directions," Int J Hyperthermia, 2002, 18(4):267-284.

(56) References Cited

OTHER PUBLICATIONS

Mountford et al, "Thermal activation of superheated lipid-coated perfluorocarbon drops," Langmuir, 2015, 31(16):4627-4634.

Moyer et al., "High-intensity focused ultrasound ablation enhancement in vivo via phase-shift nanodroplets compared to microbubbles," J Ther Ultrasound, 2015, 3:7, 9 pp.

Nakatsuka et al., "Aptamer-Crosslinked Microbubbles: Smart Contrast Agents for Thrombin-Activated Ultrasound Imaging," Adv Mater, 2012, 24(45):6010-6016.

Okada et al., "Heterogeneous delayed enhancement of the liver after ultrasound contrast agent injection—a normal variant," Ultrasound Med Biol, 2002, 28(8):1089-1092.

Oleson et al., "Hyperthermia by Magnetic Induction: Experimental and Theoretical Results for Coaxial Coil Pairs," Radiation Research, 1983, 95(1):175-186.

Ophir et al., "Contrast agents in diagnostic ultrasound," Ultrasound Med Biol, 1990, 16:209 / Ultrasound Med Bio, 1989, 15(4):319-333.

Pankhurst et al., "Applications of magnetic nanoparticles in biomedicine," J Phys D, Applied Physics, 2003, 36:R167-181.

Reilly, "Principles of Nerve and Heart Excitation by Time-varying Magnetic Fields," Annual NY Academy of Science, 1992, 649:96-117.

Reiss, "Understanding the Fundamentals of Perfluorocarbons and Perfluorocarbon Emulsions Relevant to in Vivo Oxygen Delivery," Artif Cells Blood Substit Immobil Biotechnol, 2005, 33:47-63.

Righi et al., "Peptide-based coatings for flexible implantable neural interfaces," Sci Rep, 2018, 8(1):502, 14 pp.

Robbin et al., "Perflenapent emulsion: a US contrast agent for diagnostic radiology—multicenter, double-blind comparison with a placebo," EchoGen Contrast Ultrasound Study Group, Radiology, 1998, 207(3):717-722.

Rosensweig, "Heating magnetic fluid with alternating magnetic field," J Magn and Magn Materials, 2002, 252:370-374.

Samuel et al., "In vivo microscopy of targeted vessel occlusion employing acoustic droplet vaporization," Microcirculation, 2012, 19(6):501-509.

Schutt et al., "Injectable microbubbles as contrast agents for diagnostic ultrasound imaging: the key role of perfluorochemicals," Angew Chem Int Ed Engl, 2003, 42(28):3218-3235.

Sheeran et al., "Decafluorobutane as a Phase-Change Contrast Agent for Low-Energy Extravascular Ultrasonic Imaging," Ultrasound Med Biol, 2011, 37(9):1518-1530.

Shinkai et al., "Targeting Hyperthermia for Renal Cell Carcinoma Using Human MN Antigen-specific Magnetoliposomes," Jpn J Cancer Res, 2001, 92:1138-1146.

Shinkai et al., "Effect of Functional Magnetic Particles on Radiofrequency Capacitive Heating: An in vivo Study," Jpn J Cancer Res, 2002, 93:103-108.

Simberg et al., "Targeting of perfluorocarbon microbubbles to selective populations of circulating blood cells," J Drug Target, 2009, 17(5):392-398.

Suzuki et al., "Anticancer effect and immune induction by hyperthermia of malignant melanoma using magnetite cationic liposomes," Melanoma Res, 2003, 13(2):192-135.

Tempany et al., "MR Imaging-guided Focused Ultrasound Surgery of Uterine Leiomyomas: A Feasibility Study," Radiology, 2003, 226:897-905.

Tiemann et al., "Stimulated Acoustic Emission Nonbackscatter Contrast Effect of Microbubbles Seen with Harmonic Power Doppler Imaging," Echocardiography, Jan 1997, 14(1):65-70.

Weller et al, "Ultrasound Imaging of Acute Cardiac Transplant Rejection With Microbubbles Targeted to Intercellular Adhesion Molecule-1," Circulation, 2003, 108:218-224.

Whitehead et al., "Artificial Membrane Fusion Triggered by Strain-Promoted Alkyne-Azide Cycloaddition," Bioconjug Chem, 2017, 28(4):923-932.

Wu et al., "Focused Ultrasound-Facilitated Brain Drug Delivery Using Optimized Nanodroplets: Vaporization Efficiency Dictates Large Molecular Delivery," Phys Med Biol, 2018, 63(3):035002, 24 pp.

* cited by examiner

| Formulation | PFC | Size (μm) | Concentration (#/mL) |
|---|---|---|---|
| MB (C22:0) | PFB | $1.63 \pm 0.01^a$ | $2.6 \times 10^9 \pm 1.3 \times 10^{8a}$ |
| MB (C18:0) | PFB | $1.9 \pm 0.02^a$ | $1.2 \times 10^9 \pm 4.9 \times 10^{7a}$ |
| MB (C16:0) | PFB | $1.7 \pm 0.01^a$ | $5.9 \times 10^9 \pm 1.4 \times 10^{8a}$ |
| MB (C18:0) | PFB | $2.92 \pm 0.02^a$ | $5.9 \times 10^8 \pm 2.83 \times 10^{7a}$ |
| MB (Albumin) | PFB | $1.0 \pm 0.01^a$ | $5.7 \times 10^9 \pm 3.3 \times 10^{8a}$ |
| NBs (C18:0) | PFB | $0.448 \pm 0.17^b$ | |
| | | $0.280 \pm 0.02^c$ | $8.7 \times 10^{10} \pm 5.5 \times 10^{10c}$ |
| ND (C22:0) | PFB | $0.450 \pm 0.003^b$ | |
| | | $0.292 \pm 0.04^c$ | $9.4 \times 10^{11} \pm 2.6 \times 10^{11c}$ |
| ND (C18:0) | PFB | $0.236 \pm 0.05^b$ | |
| | | $0.250 \pm 0.02^c$ | $2.5 \times 10^{11} \pm 9.3 \times 10^{10c}$ |
| ND (C18:0) | PFP | $0.260 \pm 0.03^b$ | |
| | | $0.255 \pm 0.03^c$ | $7.3 \times 10^{11} \pm 4.0 \times 10^{11c}$ |
| ND (C16:0) | PFB | $0.277 \pm 0.09^b$ | |
| | | $0.272 \pm 0.05^c$ | $3.2 \times 10^{11} \pm 2.0 \times 10^{11c}$ |
| ND (C18:0) | PFH | $0.270 \pm 0.025^b$ | |
| | | $0.244 \pm 0.02^c$ | $6.6 \times 10^{11} \pm 1.2 \times 10^{11c}$ |

Initial MB and ND size and concentrations determined by Multisizer[a], DLS[b] and TRPS[c]

FIG. 28

MICROBUBBLE AND NANOBUBBLE EXPANSION USING PERFLUOROCARBON NANODROPLETS FOR ENHANCED ULTRASOUND IMAGING AND THERAPY

CROSS-REFERENCE TO RELATED APPLICATIONS

This application claims priority to U.S. Provisional Patent Application Ser. No. 62/809,280 filed Feb. 22, 2019, the entire contents of which are incorporated herein by reference, including the appendices attached thereto.

BACKGROUND

A. Field

This disclosure relates to imaging and therapy techniques comprising nanodroplets. More particularly, embodiments of the disclosure relate to the use of nanodroplets to inflate nanobubbles or microbubbles to provide improved imaging and/or therapeutic aspects.

B. Related Art

Various techniques have been developed to image and provide therapy to conditions that require medical treatment, including for example, cancerous tumors. Certain techniques incorporate the use of gaseous bubbles to increase the visibility of regions of interest during ultrasound imaging. Acoustic droplet vaporization (ADV) requires acoustic waves to decrease local pressure of liquid perfluorocarbon (PFC) below its vapor pressure to trigger its phase transition from liquid to gas. Although promising, this field remained stagnant despite the introduction of novel formulations of low-boiling point (<0° C.) perfluorocarbon (PFC) nanodroplets (NDs) that are superheated at body temperature. This is most likely due to the larger ND dose needed compared to microbubbles (MBs), the inability to vaporize all NDs, the amount of phospholipid surfactant that is insufficient to properly stabilize newly formed MBs that are five times larger, and the spontaneous uncontrolled vaporization of ND that could lead to potential toxicity.

Neat perfluorocarbon (PFC) and emulsions of PFC exhibit exceptional properties such as high thermal stability and chemical inertness owing to the unique characteristics of fluorine (F) and the carbon-fluorine (C—F) linkage—the strongest covalent bond in organic chemistry. PFC in its liquid state is often considered gas-like fluid as it displays low intermolecular cohesiveness due to the low polarizability of F, which results in lower Van der Waals (VdW) interactions between pairs of $CF_2$ as opposed to VdW interactions between pairs of $CH_2$. More importantly, PFC have additional interrelated key properties that are critical for clinical translation, including biocompatibility, high purity, low surface tensions, high fluidity as well as high vapor pressure and gas solubility compared to hydrocarbons of similar molecular mass (1). In addition, low molecular weight PFC are rapidly excreted by exhalation for PFC with no side effects.

Owing to their unique ultrasound (US) backscattered signal, single PFC gas-filled microbubbles (MBs) (2, 3) or single MB-labeled cells (4) can be detected in vivo using a clinical US system. This unique US response of PFC gas-filled MBs has prompted the development of a variety of new US contrast agents and has increased the possibility of diagnostic imaging worldwide. However, other than altering ligands on the MBshell to target specific tissues, translatable MB-based discoveries as US contrast agents have been stagnant for the past 2 decades, mostly because their micron size limits their distribution to the intravascular space where they can only interact with the endothelial surface (5, 6), circulating cells (7), or blood clots (8, 9).

Nanoscale particles exhibit several advantages for molecular imaging over MBs. Because of their 100-300 nm size, PFC nanodroplets (NDs) are able to leak into the tumor extracellular space (1). In addition, their larger particle count, greater resilience to US and longer in vivo dwell time are expected to improve targeting efficiency of NDs over MBs to intravascular sites in addition to extravascular sites. However, the key impediment of NDs is their lesser echogenicity and thus lesser US contrast compared to MBs due to their limited reflectivity and compressibility (10), requiring large doses that potentially increase side-effects (11). While their backscatter is indistinguishable from tissues, NDs are able to phase change into MBs through a process known as of acoustic droplet vaporization (ADV) resulting in improved detection by US. ADV was introduced almost two decades ago as a potential tool to induce vascular occlusion by locally triggering local embolization on downstream tissues using micron-size perfluoropentane (PFP) filled droplets (12). However, using micron-size PFP-filled droplets potentially leads to spontaneous droplet vaporization, particularly during injection due to shear stress and cavitation, which is a concern for clinical translation (13). In addition, occlusion was accomplished exclusively in the larger arteries, resulting in undesired non-discriminant downstream embolization and side effects (14-16) or incomplete embolization for tumors still fed from smaller arteries.

While a few groups have successfully vaporized liquid low boiling point droplets of PFP (17), or perfluorobutane (PFB) (18-20) to MBs in animals, their clinical translation and widespread use has been limited by critical efficacy and safety challenges. Firstly, the acoustic energy required to vaporize droplets, particularly NDs, in humans is expected to be higher than the current FDA limit (12) because of the high Laplace pressure inside NDs, the increased interstitial pressure in tumors and the US attenuation in deep tissues (21). Secondly, the required dose of droplets or NDs is high, which potentially leads to side-effects (11). Thirdly, the inability to vaporize all NDs due to tissue attenuation, and uncontrolled spontaneous vaporization of sub-micron droplets at body temperature (13) raises safety concerns as it could lead to unwanted microvascular occlusion. Finally, red blood cell extravasation occurs following ADV-triggered capillary rupture due to initial MB expansion or most likely to the violent MB collapse associated with inertial cavitation at insonation (22). In addition to these safety concerns, MBs formed by ADV might not be stable enough for effective gas embolotherapy as they originate from NDs that are 5 times smaller (23), and thus do not have enough phospholipid surfactants to be properly stabilized. Although the presence of MBs near NDs decreases the ADV threshold (24), the same challenges remain for the clinical translation of ADV.

SUMMARY

Embodiments of the present disclosure relate to the field of medical diagnostics and therapeutics, and more specifically to the development of a new class of imaging and theranostic agents obtained by the combination of perfluorocarbon (PFC) gas filled microbubbles (MBs) and nanobubbles (NBs) with PFC liquid core nanodroplets (NDs). Particular aspects present a novel strategy for improved detection and treatment of diseased tissue. Certain aspects comprise using ultrasound contrast agents (MBs or NBs) to target intravascular and/or extravascular sites, followed by a second injection of non-targeted NDs or NDs targeted to the pre-injected MBs or NBs. In specific aspects, the PFC liquid pool of NDs may then transfer to the MBs or NBs to inflate them. Inflating MBs or NBs may increase ultrasound signal easing detection. However, inflation may be used to speed blood clot dissolution, induce tumor vascular occlusion, aid in gene delivery and transfection, and more.

The inventors have found that NDs act as a PFC and phospholipid reservoirs that transfer to the adjacent NBs or MBs, which triggers their growth. Interestingly, while both NBs and NDs individually exhibit very limited ultrasound signal on B-mode imaging when exposed to low acoustic power, their combination results in a rapid and dramatic increase in signal visible on standard ultrasound imaging. The inventors hypothesize that the low but non-negligible PFC solubility in water and high vapor pressure of PFC allow condensed PFC from the NDs to dissipate and diffuse away into the aqueous phase to reach the NB core and initiate expansion. This innovation is different from the use of NDs as phase change contrast agent (PCCA) because no sound waves are necessary to inflate the NBs or MBs but result from the large vapor pressure in the superheated nanodroplets. Such a driving force does not exist between two microbubbles with the same Laplace pressure.

The inventors have demonstrated rapid NB expansion when mixed with a concentrated solution of fluorescein-labeled NDs (~10:1 ND/NB ratio) by microscopy and ultrasound. The inventors showed evidence that the phospholipids from the ND shell were incorporated with the newly formed microbubbles (MBs) by fluorescence microscopy.

Embodiments of the present disclosure also relate to the field of in vitro rare cell isolation. More specific aspects describe a new platform that may improve cell detection sensitivity and isolation using a combination of perfluorocarbon (PFC) gas filled nanobubbles (NBs) or microbubbles (MBs) targeted to any cell surface receptor of interest, and PFC liquid nanodroplets (NDs). Particular aspects include a novel strategy to better detect and isolate cells in vitro using buoyancy. Certain aspects comprise adding targeted NBs or MBs to a cell suspension, followed by the addition of NDs that could be non-targeted or targeted to the MBs or MBs. The liquid PFC from superheated PFC NDs can then transfer to the NBs or MBs to inflate them, increase buoyancy and the floatation of MB-cell construct to ease or speed their recovery using mild or no centrifugation.

Briefly, the present disclosure provides a novel strategy to achieve the benefits of ADV, including improved detection and tumor microvascular embolization, without the need for ultrasound. Because liquid PFC in NDs is at a much higher partial pressure than its gaseous counterpart in microbubbles (MB), the coexistence of ND and MB leads to PFC vaporization and transfer into MB leading to their expansion. The thermodynamic driving force is the large vapor pressure for the nanodroplets, which are highly superheated. Such a driving force does not exist between two microbubbles with the same Laplace pressure. The extent of the MB expansion was quantified by counting and measuring the size of expanded microbubbles with microscopy and flow cytometry. This MB expansion process was applied to expand poorly echogenic nanobubbles (NBs) to larger MBs and resulted in a 4-fold ultrasound signal enhancement after 30 seconds of incubation at 37° C. The inventors have demonstrated that the rate and extent of expansion were affected by the type of PFC used, MB size, length and type of lipid emulsifier that has an effect on both interfacial tension and the ability of bubbles to expand. Finally, MB inflation was demonstrated in vitro in tubing flow system and in two animal models. First, MBs and ND were both injected subcutaneously in the ear of a mouse to demonstrate MB expansion in vivo using intravital microscopy. In a second animal model, MC38 colon cancer cells were implanted in the flank of a mouse and MC38-targeting MBs and NDs were injected intravenously in sequence to demonstrate tumor targeting and MB inflation at the tumor site using microscopy.

Certain embodiments include a method of imaging a region of interest, where the method comprises: providing bubbles to the region of interest; providing nanodroplets to the region of interest; increasing the average bubble diameter of the bubbles while the bubbles are in the region of interest; and exposing the region of interest to an ultrasound stimulus to generate an image of the region of interest.

Certain embodiments include a method to safely occlude tumor microvessels non-invasively and without the need for ultrasound, where the method comprises: providing bubbles to the region of interest, diameter between 200 nm and 10 µm; providing nanodroplets to the region of interest; increasing the average bubble diameter of the bubbles while the bubbles are in the region of interest.

In particular embodiments, providing the nanodroplets to the region of interest is performed subsequent to providing the bubbles to the region of interest. In some embodiments, the bubbles and the nanodroplets are provided to the region of interest in a composition comprising the bubbles and the nanodroplets. In specific embodiments, the average bubble diameter of the bubbles is increased by an order of magnitude when the bubbles are in the region of interest. In certain embodiments, the average bubble diameter of the bubbles is increased by up to two orders of magnitude when the bubbles are in the region of interest. In particular embodiments, the nanodroplets comprise a perfluorocarbon (PFC).

Specific embodiments include a method of increasing bubble size, where the method comprises: providing bubbles to a first region, wherein the bubbles have an average bubble diameter between 200 nm and 10 µm; providing nanodroplets proximal to the bubbles; and increasing the average bubble diameter of the bubbles while the bubbles are in the first region. In certain embodiments, providing the nanodroplets proximal to the bubbles is performed subsequent to providing the bubbles to the first region. In particular embodiments, the bubbles and the nanodroplets are provided in a composition comprising the bubbles and the nanodroplets. In some embodiments, the average bubble diameter of the bubbles is increased by an order of magnitude when the bubbles are in the region of interest.

Particular embodiments include a method of isolating a cell population in blood or media, where the method comprises: providing bubbles to a region of interest, wherein the bubbles are coupled to targeted cell structures within the region of interest; providing nanodroplets to the region of interest; increasing the average bubble diameter of the bubbles and increasing the buoyancy of the bubbles while the bubbles are coupled to the targeted cell structures within the region of interest; and isolating the bubbles and targeted cell structures within the region of interest from non-targeted cell structures within the region of interest.

In certain embodiments, isolating the bubbles and targeted cell structures within the region of interest from non-targeted cell structures within the region of interest comprises floating the bubbles and targeted cell structures within the region of interest. In particular embodiments, providing the nanodroplets to the region of interest is performed subsequent to providing the bubbles to the region of interest. In some embodiments, the bubbles and the nanodroplets are provided to the region of interest in a composition comprising the bubbles and the nanodroplets. In specific embodiments, the average bubble diameter of the bubbles in increased by an order of magnitude when the bubbles are in the region of interest. In certain embodiments, the nanodroplets comprise a perfluorocarbon (PFC).

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 28 illustrates a table of initial MBs, NBs and NDs size and concentration used in testing.

DETAILED DESCRIPTION OF THE INVENTION

An overview of exemplary embodiments of the present disclosure will be presented initially, followed by further discussion of specific aspects.

Figure 1:
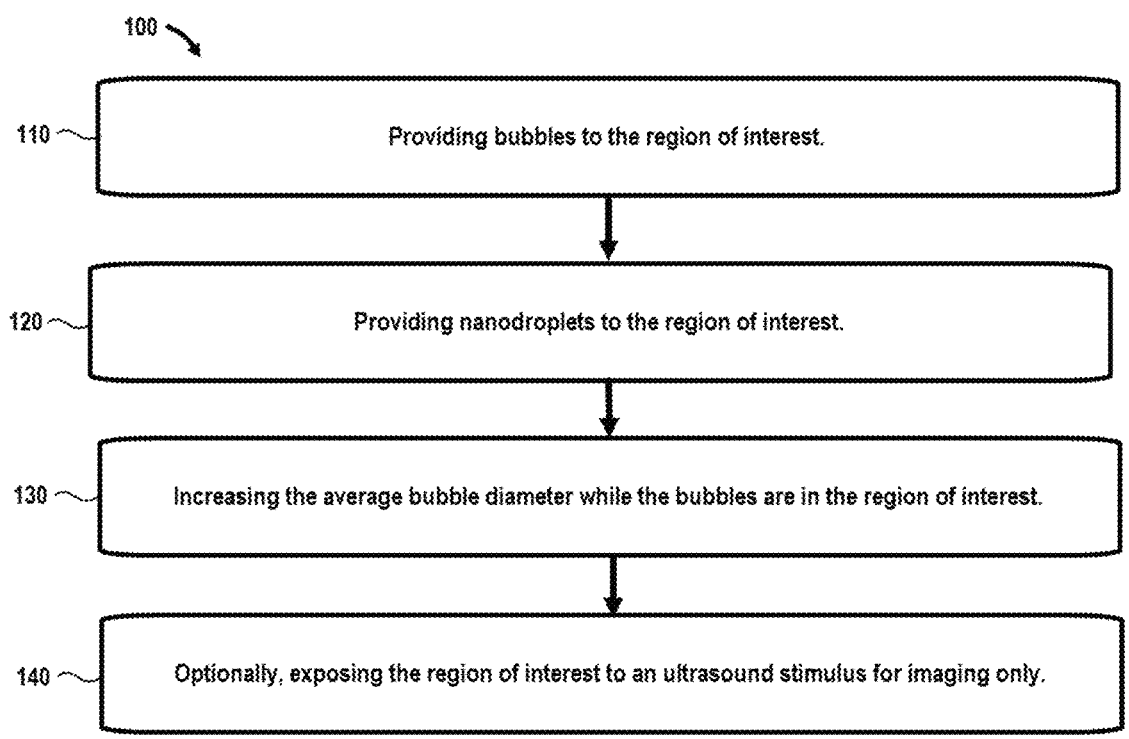
FIG. 1 illustrates a flowchart of steps in a method that can be used in ultrasound imaging techniques according to an exemplary embodiment of the present disclosure.

Referring initially to FIG. 1, a flowchart 100 illustrates steps in a method that can be used in ultrasound imaging techniques. In this embodiment, step 110 comprises providing bubbles to the region of interest. In certain embodiments, the bubbles may be nanobubbles or microbubbles with an average bubble diameter between around 200-600 nm (nanobubbles) and 1-10 μm (microbubbles).

Figure 10:
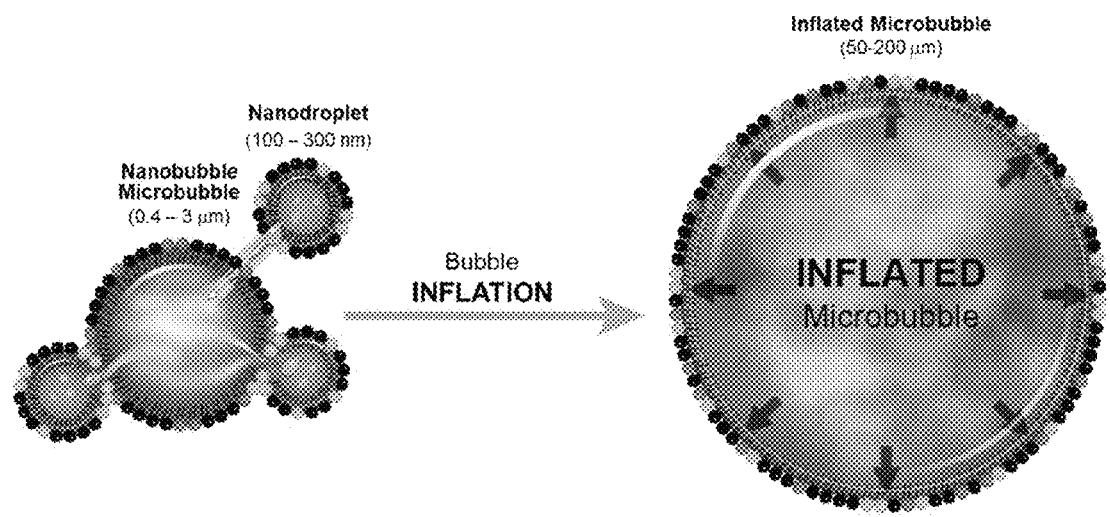
FIG. 10 illustrates a schematic representation of the nanodroplet-microbubble gas and phospholipid exchange.

To circumvent the challenges of ADV for effective gas embolotherapy, the inventors took inspiration from a biological process and the second law of thermodynamics: the process by which PFC is eliminated from the body by exhalation (25). When PFC liquid emulsions or PFC gas-filled MBs traverse the alveolar capillaries, PFC transfers to the air-filled alveolar space because of the large partial pressure gradient (1). In addition, since liquid PFC in NDs is at a much higher partial pressure and interfacial pressure (assuming equal interfacial tension) than its gaseous counterpart in the MBs, the inventors hypothesized that when micron-scale or sub-micron-scale MBs are in close proximity to nanoscale liquid PFC NDs, PFC vapor transfers from the NDs to MBs and expands them (Laplace Law). Although PFC solubility in water is low, it is not negligible. The inventors speculate that PFC molecules would diffuse out of NDs, move freely between water molecules surrounding the NDs, and reach the adjacent MB core, as vaporized PFC has higher entropy than its liquid state. A schematic representation of the nanodroplet-microbubble gas exchange shown is in FIG. 10 (where σ=interfacial tension). This expansion phenomenon, also aided by the transfer of air from plasma due to the osmotic gradient (13), results in large MBs that can embolize vessels without US activation. There are a few examples of not fully understood phenomena in the literature that the inventors believe the inventors can partly explain with aspects of the present disclosure. Fowlkes et al. demonstrated optically vessel occlusion through ADV using intravital microscopy on the rat cremaster muscle (22). In this study, the size of lodged MBs was bigger than the predicted 5× increase in diameter, as 2 μm diameter droplets vaporized into 76 μm mean length×36 μm mean diameter or 25 μm mean length×11 μm mean diameter, respectively when the vaporization was triggered in the capillaries (4-7 μm) or in a larger arteriole (~125 μm). While the authors hypothesized that MBs coalescence will happen more in capillaries where the flow velocity is smaller than in the feeder vessel, the inventors also believe that PFC transfer from unvaporized NDs contribute to MB inflation. In the clinic, the first heterogenous delayed enhancement of the liver due to the formation of larger MB after injection of contrast agents (Levovist and Echogen) has been reported by Wolf et al. with no precise causes nor mechanism (26). Interestingly, the phenomenon was described by others with different gas and shell types. Cardinale et al. hypothesized that MB slowing down in the hepatic sinusoids inflated with gas from the intestinal microcirculation by osmotic effect (27), as the effect was not observed when patients received a second dose 24 h later (26, 27) or 9 days later (27).

The inventors believe that this new US-based approach will lead to the development of new tools to better treat and detect disease. Of the many possible applications of this novel platform, which is beyond the scope of this report, the inventors believe the inventors can induce microvascular embolization as was originally intended for ADV, but at a much smaller dose and without the need for US vaporization. Starving cancer cells to death by restricting their blood supply was proposed nearly 50 years ago. Recently, systemic treatment with anti-angiogenesis therapy that is directed against immature tumor microvessels (28) has offered short term benefits with limited impact on patient survival, mostly because it has inhibited tumor growth rather than killing established ones. In addition, some major concerns remain such as tumor resistance, and side effects due to the inhibition of normal angiogenesis. Alternatively, mechanical occlusion or embolization, although less discriminant, has been used effectively to treat hepatocellular and renal cancers. This procedure is achieved by introducing plain or drug eluting embolic material through a catheter that is advanced as close as possible to the tumor feeding. While effective, this procedure is not tumor-specific, is invasive and carries the typical risks linked to angiography. In addition, because tumors can parasitize other arteries, embolization may be incomplete. As of today, there is no effective strategy to achieve total occlusion of the tumor microvasculature, particularly in a non-invasive manner. Expanding MBs using droplet vaporization to microembolize tumor vasculature without the need for acoustic activation has the potential to be translated in the clinic.

In the embodiment shown in FIG. 1, method 100 comprises an aspect 110 of providing bubbles to the region of interest. In certain embodiments, the bubbles may have an average bubble diameter between around 200-600 nm (nanobubbles) and 1-10 μm (microbubbles). Method 100 also comprises an aspect 120 of providing nanodroplets to the region of interest. In certain embodiments, the bubbles in aspect 110 and the nanodroplets in aspect 120 can be introduced to the region of interest via sequential injections (e.g. an initial injection of bubbles, followed by a subsequent injection of nanodroplets). In specific embodiments, the nanodroplets may comprise a perfluorocarbon (PFC). Method 100 further comprises an aspect 130 of increasing the average bubble diameter of the bubbles while the bubbles are in the region of interest. As explained in further detail below, the average diameter of the bubbles can be increased (e.g. the bubbles can be further "inflated") via the transfer of perfluorocarbons and phospholipids from the nanodroplets to the bubbles. In certain embodiments, the volume of the bubbles can be increased by up to 6 orders of magnitude. Method 100 also comprises an aspect 140 of optionally exposing the region of interest to an ultrasound stimulus (e.g. in order provide imaging for the region of interest). The increased average bubble diameter discussed in aspect 130 can yield improved images by providing a stronger response signal to the ultrasound stimulus.

Figure 2:
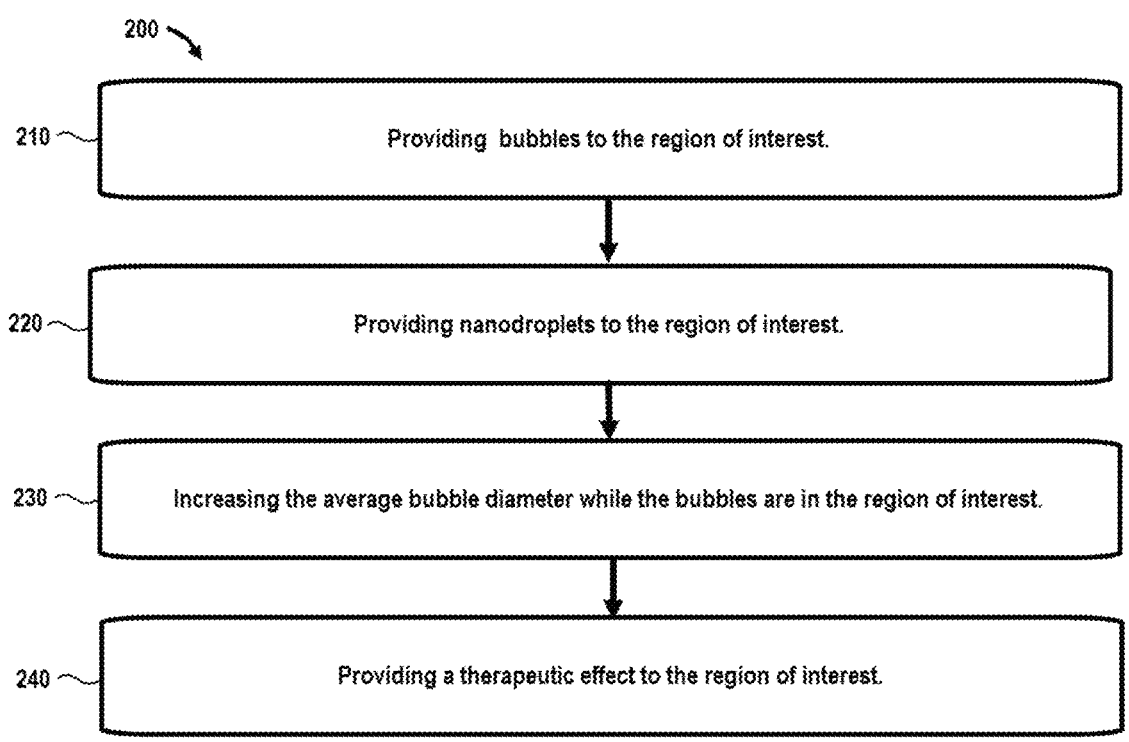
FIG. 2 illustrates a flowchart of steps in a method for providing a therapeutic effect to a region of interest.

Referring now to FIG. 2, an overview of another method 200 for providing a therapeutic effect to a region of interest. Method 200 comprises aspects 210, 220, and 230 that are generally equivalent to aspects 110, 120 and 130 previously discussed in method 100 above. Accordingly, for sake of brevity, the specifics of these aspects will not be repeated here. Method 200, however, further comprises an aspect 240 of providing a therapeutic effect to the region of interest. In certain embodiments, the therapeutic effect can be provided by utilizing the increased diameter of bubbles with a specific tumor target to achieve occlusion of the tumor microvasculature, effectively reducing the blood flow to the tumor.

Figure 3:
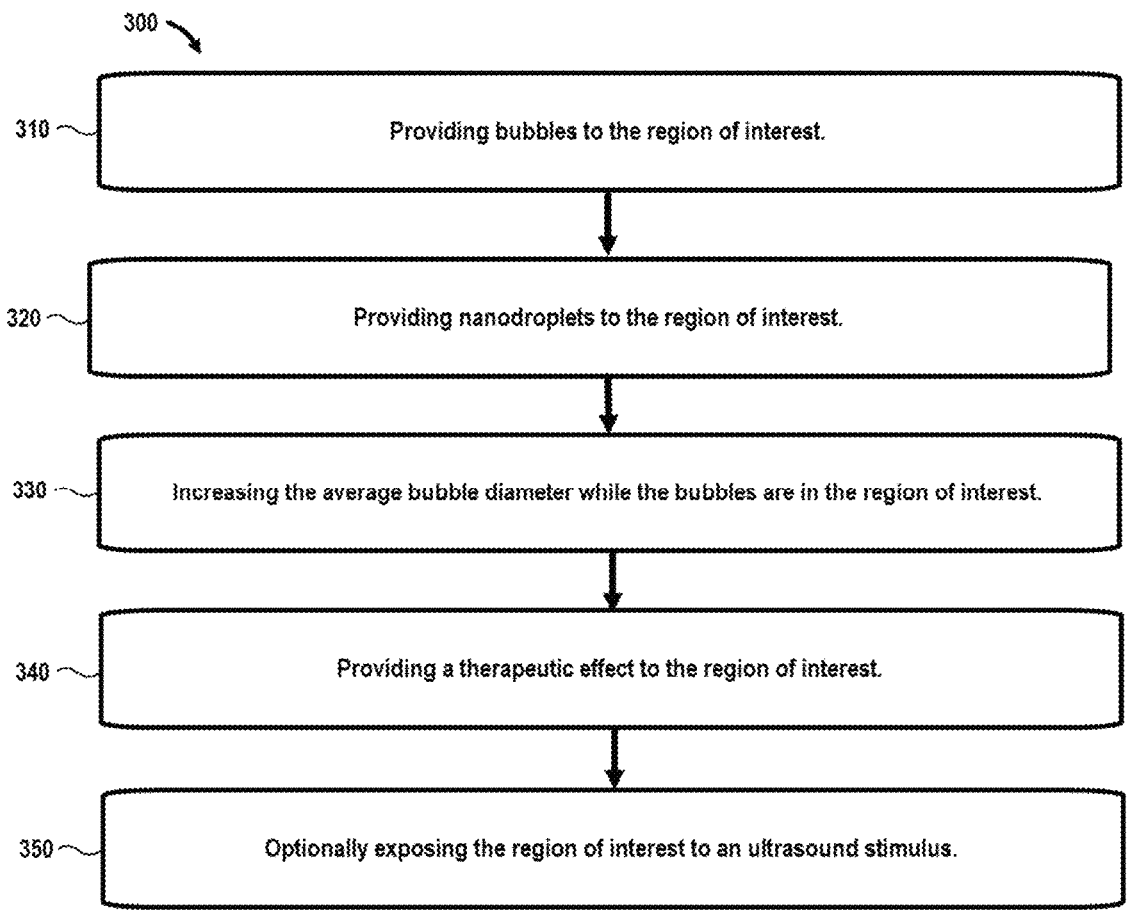
FIG. 3 illustrates a flowchart of steps in a method that combines aspects of imaging method and treatment.
Figure 4:
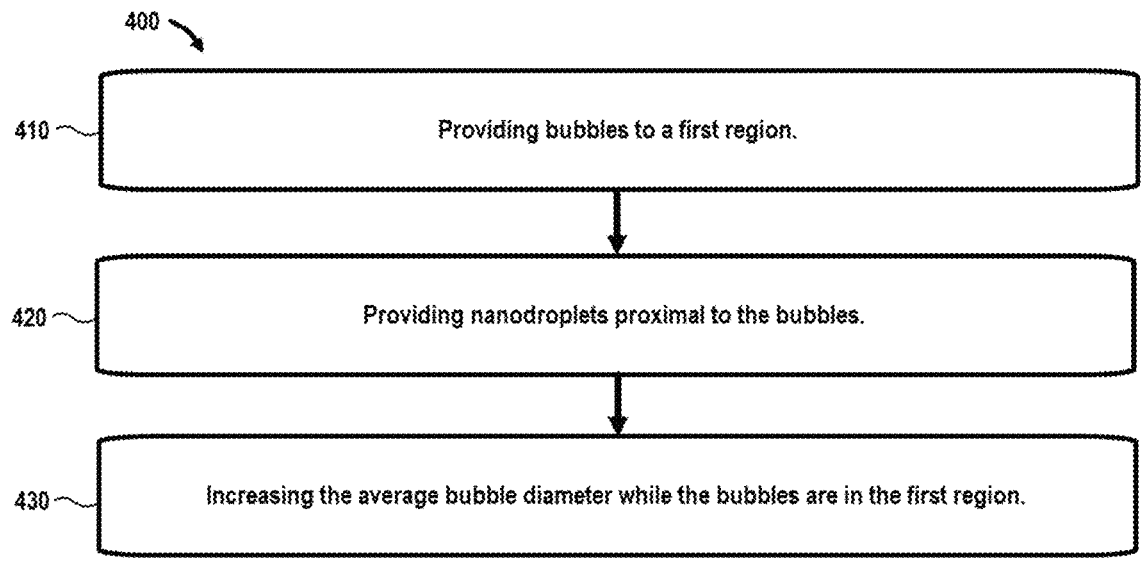
FIG. 4 illustrates a flowchart of steps in a method for increasing an average bubble diameter, without specification to imaging or therapeutic aspects.

Referring now to FIG. 3, an overview of a method 300 is provided that combines aspects of imaging method 100 and treatment (e.g. providing therapeutic effect) method 200. Specifically, aspects 310, 320 and 330 are equivalent to aspects 110, 120 and 130 previously discussed in method 100 above, while aspect 340 comprises providing a therapeutic effect to the region of interest and aspect 350 comprises optionally exposing the region of interest to an ultrasound stimulus (e.g. for use in ultrasound imaging). Referring now to FIG. 4, an overview of a method 400 is provided for increasing an average bubble diameter, without specification to imaging or therapeutic aspects. This embodiment comprises aspects 410, 420 and 430 that are equivalent to aspects 110, 120 and 130 previously discussed in method 100 above.

Figure 5:
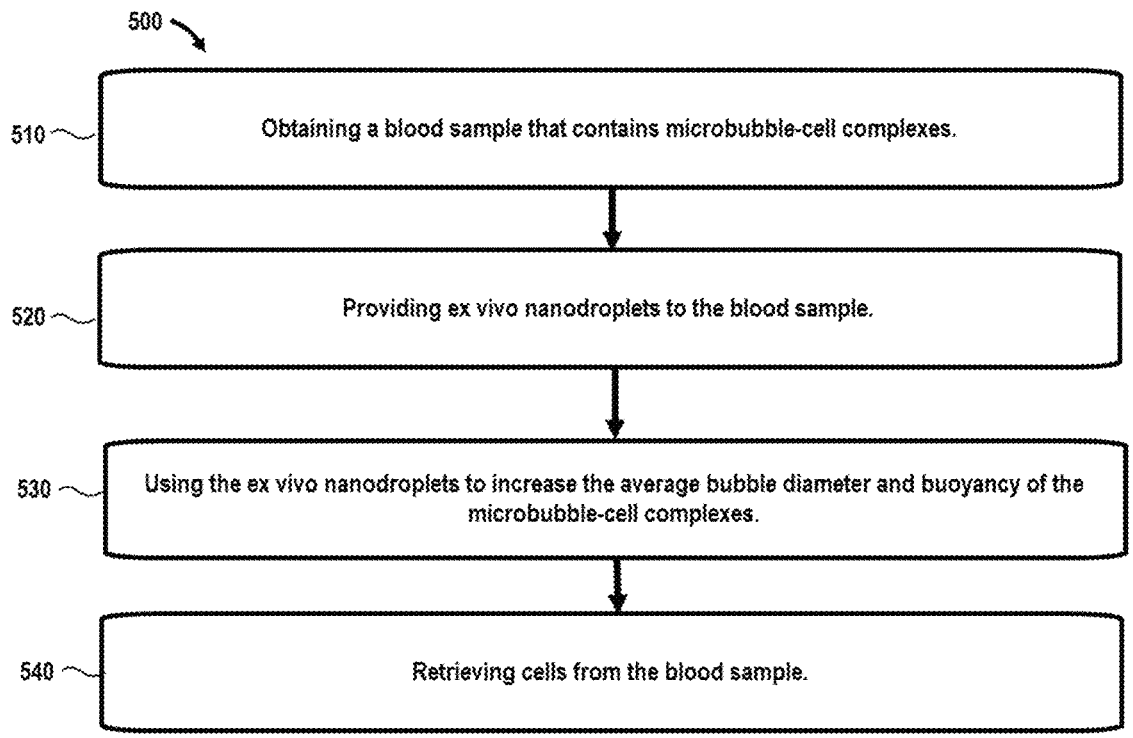
FIG. 5 illustrates a flowchart of steps in a method for using ex vivo nanodroplets to increase the average bubble diameter and buoyancy of the microbubble-cell complexes in a blood sample

Aspects of the present disclosure also relate to methods where the increased buoyancy of the bubbles can be used to isolate bubbles and targeted cell structures. Referring now to FIG. 5, a method 500 includes an aspect 510 that comprises obtaining a blood sample that contains microbubble-cell complexes. Method 500 also comprises an aspect 520 of providing ex vivo nanodroplets to the blood sample. In addition, method 500 includes an aspect 530 of using the ex vivo nanodroplets to increase the average bubble diameter and buoyancy of the microbubble-cell complexes. Method 500 further comprises aspect 540 of retrieving cells from the blood sample.

Referring back now to particular aspects of the present disclosure discussed in FIGS. 1-4, the inventors have found that NDs act as a PFC and phospholipid reservoirs that transfer to the adjacent NBs or MBs, which triggers their growth. Interestingly, while both NBs and NDs individually exhibit very limited ultrasound signal on B-mode imaging when exposed to low acoustic power, their combination results in a rapid and dramatic increase in signal visible on standard ultrasound imaging. The inventors hypothesize that the very poor water solubility and high vapor pressure of PFC allow condensed PFC from the NDs to dissipate and diffuse away into the aqueous phase to reach the NB core and initiate expansion. This innovation is different from the use of NDs as phase change contrast agent (PCCA) because no sound waves are necessary to inflate the NBs or MBs.

Figure 6:
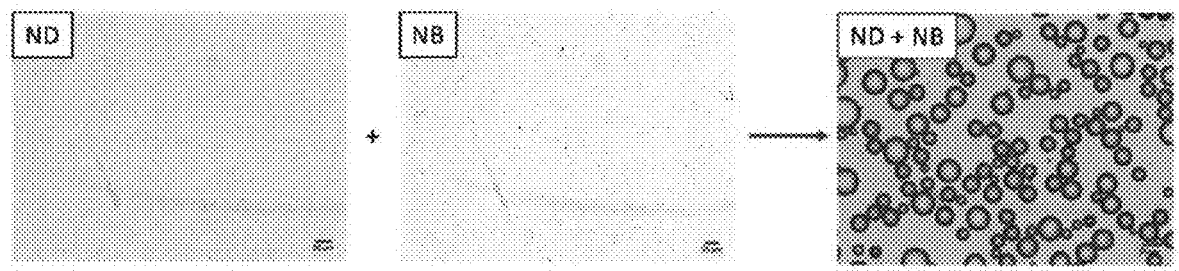
FIG. 6 illustrates representative bright field images of NDs and NBs prior and after mixing at 20× magnification.
Figure 7:
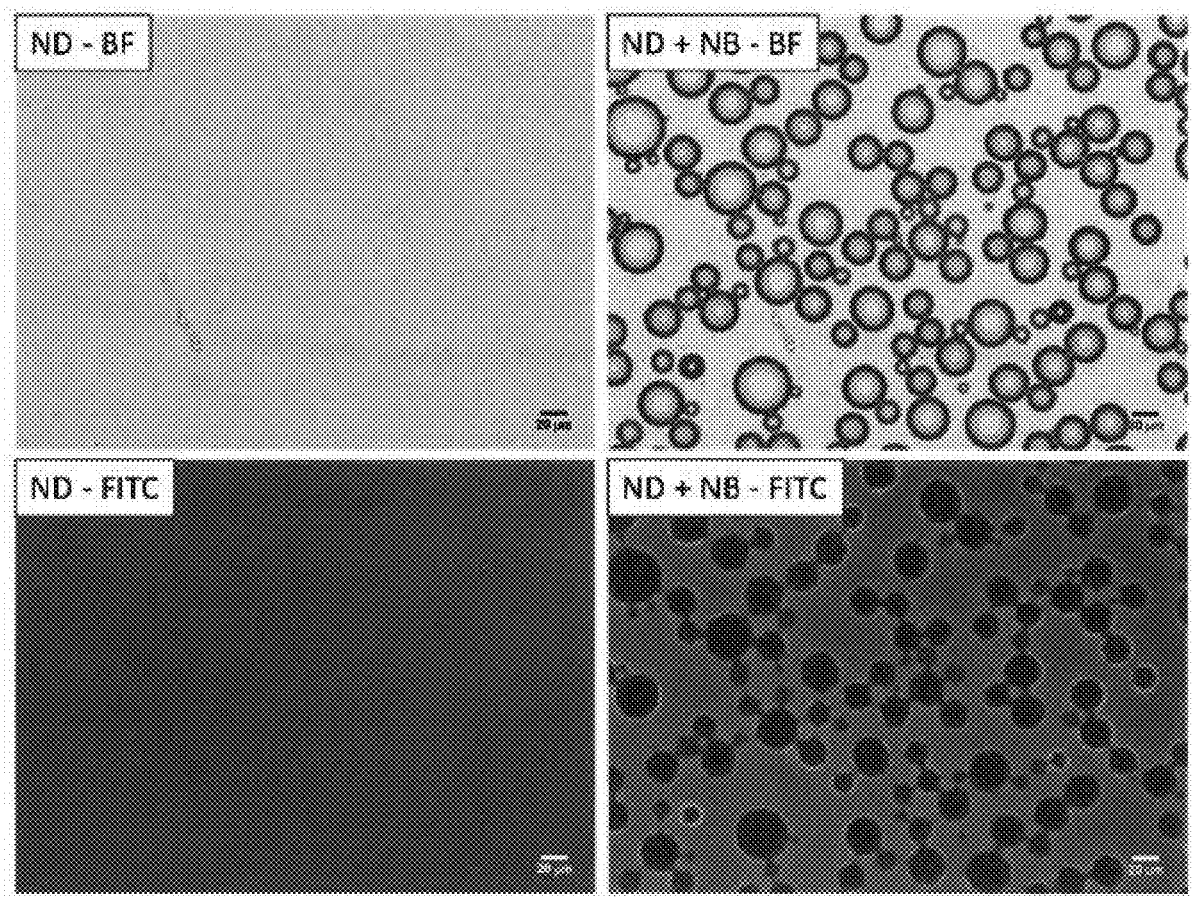
FIG. 7 illustrates representative bright field and fluorescence images of NDs before and after mixing with NBs at 20× magnification.

The inventors have demonstrated rapid NB expansion when mixed with a concentrated solution of fluorescein-labeled NDs (~10:1 ND/NB ratio) by microscopy (shown in FIGS. 6 and 7). The inventors have showed evidence that the phospholipids from the ND shell were incorporated with the newly formed microbubbles (MBs) by fluorescence microscopy.

FIG. 6 shows representative bright field images of NDs and NBs prior and after mixing at 20× magnification. Note that even if NDs and NBs have similar diameters, NDs cannot be distinguished as the refractive index of liquid perfluorobutane is close to the refractive index of water, and importantly, NB and ND s are not visible because of the microscope resolution. Upon mixing on the microscopy slide, 5-20 µm MBs were observed instantaneously (ND+NB). Scale bar is 20 µm.

FIG. 7 shows representative bright field and fluorescence images of NDs before and after mixing with NBs at 20× magnification. Note that post mixing (ND+NB), newly generated MBs show higher fluorescence intensity in their shell, compared to the background fluorescence from the NDs, which indicates that fluorescein labeled phospholipids (DSPC-PEG2Kfluorescein) have been incorporated in the MBs shell. Scale bar is 20 µm.

Figure 8:
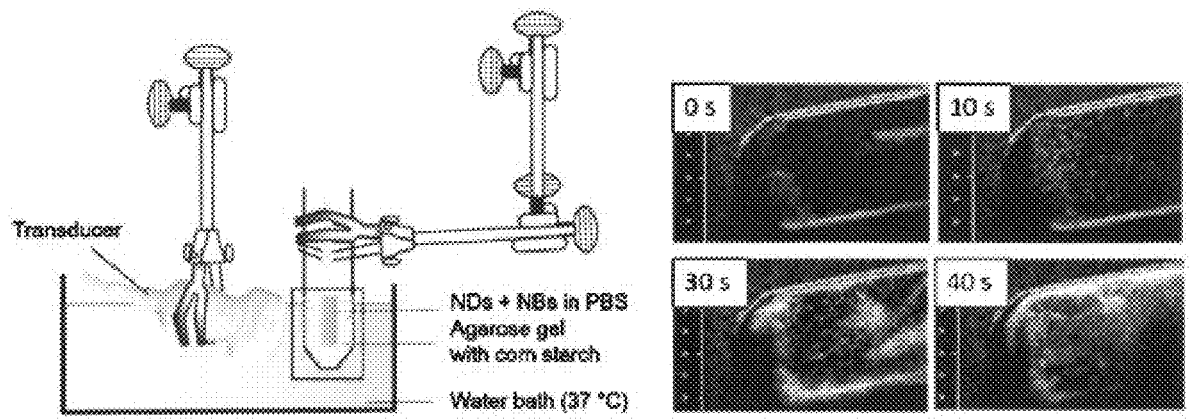
FIG. 8 illustrates a schematic representation of a one-compartment experimental setup.

FIG. 8 shows a schematic representation of the one-compartment experimental setup (left). NB expansion was observed after less than 10 seconds after addition of the NDs in the NB solution. Note that the NBs alone (0 s) only exhibit a low contrast enhancement compared to MBs (10, 30 and 40 s). Mixing NBs and NDs resulted in a marked enhancement on B-mode US imaging.

Figure 9:
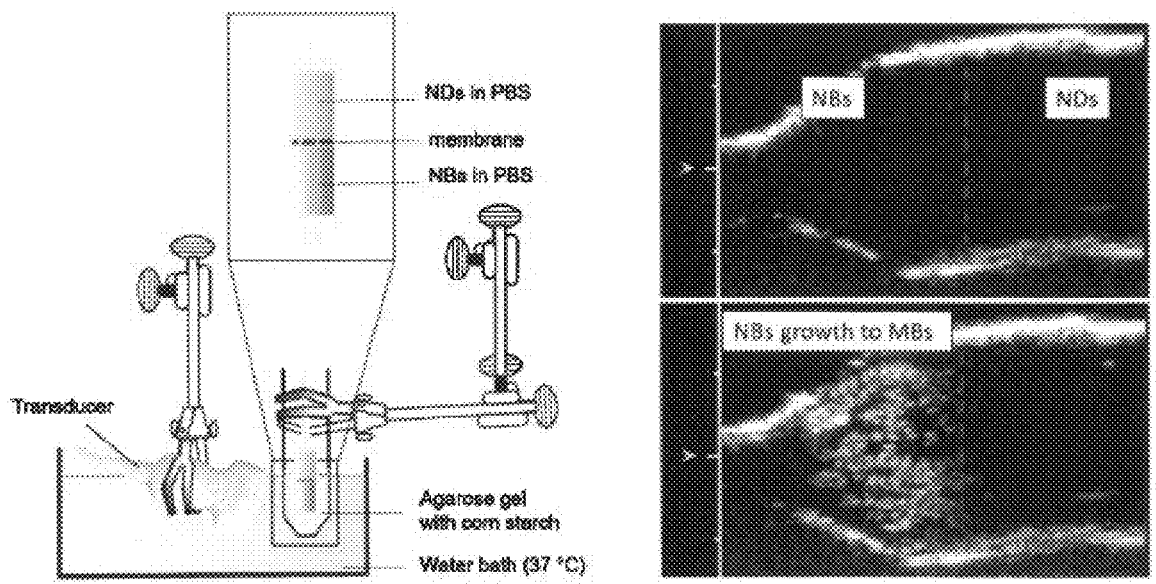
FIG. 9 illustrates shows a schematic representation of a two-compartment experimental setup.

FIG. 9 shows a schematic representation of the two-compartment experimental setup (left). Briefly, two-bulb compartments were done by cutting plastic bulbs and joining them together with a dialysis membrane in between and with parafilm to seal the system. Thirty seconds after addition of NDs in the upper compartment (right on ultrasound), NBs in the lower compartment (left on ultrasound) expanded to MBs producing a high contrast-to-noise ratio on B-mode US imaging. As expected, no acoustic droplet vaporization was observed in the upper ND compartment as they were exposed to the lowest ultrasound transmit power (MI=0.05, PNP=0.13 MPa.

Referring now to aspects of the present disclosure that relate to improvements on the current cell isolation buoyancy method using targeted MBs, the inventors have demonstrated in vitro that the addition of liquid PFC NDs (300 nm) to a MB (0.5-10 µm) suspension dramatically expands the gas bodies by up to 6 orders of magnitude, and does so without direct contact. NDs act as a PFC and phospholipid reservoirs that transfer to the adjacent NBs or MBs to trigger their growth. According to one aspect of the present disclosure, the number of attached MBs per cell required to induce buoyancy and cell recovery could decrease significantly, as only one attached MB could potentially grow to become 100 µm. This aspect can improve upon the buoyancy technique used to isolate cells. It can also be applied in vivo, by administering the NBs or MBs intravenously targeted to a circulating cell surface receptor of interest, and then adding the liquid PFC to an extracted blood sample to detect the targeted cells. Aspects of the present disclosure can improve upon existing technology in at least two ways: (1) Increasing buoyancy using PFC transfer from superheated PFC NDs will decrease the number of MB per cell needed to cause cells to float; and (2) targeted NBs that are more effective at locating their target both in vitro and particularly in vivo, and allow the accumulation of more NBs at the cell surface, can also induce attached cells to float when they are inflated by the liquid PFC.

The current standard for cell isolation is to target magnetic beads to the cell surface receptor of interest that can only be done in vitro and requires special equipment for isolation and then cell handling to remove the magnetic beads. The use of buoyancy to isolate cells improves upon the magnetic bead strategy by not requiring MB removal after isolation, simplifying the isolation technique, and adding the potential of administering the MBs intravenously to search for circulating cells of interest prior to isolation.

Aspects of the present disclosure can provide a solution to when not enough MBs attach to the cell of interest to make it buoyant, or if NBs are used to improve cell interaction but the total gas bodies remain insufficient to cause attached cells to float. When a blood sample or any cell or particle suspension that contains the NBs or MBs attached to cells or particles that need to be isolated is spiked with liquid PFC, preferably as an emulsion of superheated PFC ND such as PFB ND that may be targeted or non-targeted to the attached NBs or MBs, the gas bodies will inflate because of their lower PFC pressure, increasing buoyancy and causing the attached cells/particles to float. This new strategy should improve the detection limits of cells or particles in any suspension.

With typical existing techniques, the buoyancy of cells or particles to be detected or isolated depends on the number and size of MBs attached to their surface to overcome the gravitational force exerted on the attached cell or particle. This can be a limitation that severely impacts detection sensitivity when using buoyancy for isolation. Aspects of the present disclosure addresses this problem and improves the sensitivity of isolation by simply adding liquid PFC, preferably as emulsion of superheated PFC ND such as PFB ND, to inflate the attached MBs or NBs, increasing the force to overcome the gravitational force increasing buoyancy and improving cell isolation.

Unlike magnetic bead isolation, aspects of the present disclosure can be used in vivo to search for the rare circulating cells, and do not require cell manipulation to remove the beads after they are isolated. Unlike current buoyancy techniques, aspects of the present disclosure will allow the use of NBs that are more efficient at targeting, and can overcome the gravitational force for large cell or particle masses, by inflating the gas bodies attached to the cell or particle surface. For therapy, there are several schemes that this technology offers that could be exploited. These are merely some potential scenarios out of several. One potential method is the ease by which a large payload can be placed either within or attached on the shell of the droplets as compared to microbubbles. These droplets either passively or actively targeted or by merely passing through the site of interest carried by blood can be induced into phase-transition by the variety of techniques mentioned above.

Further description and explanation of the operating principles can also be found in the discussion of the example and results that follow.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

The important number of diseases diagnosed at a late stage because of absence of symptoms is objective evidence that there is a need to extend the toolbox of imaging agents to improve early detection of disease. This work demonstrates for the first time that the addition of liquid PFC NDs to a suspension containing MBs or nanobubble (NBs) leads to the dramatic expansion of the gas bodies by at least 2 and up to 6 orders of magnitudes and does so without requiring direct contact between NDs and MBs or NBs. Additional advantages of our method compared to ADV is that smaller droplets not only exhibit greater stability as they are subject to higher Laplace Pressure but will also ease inflation as the difference in interfacial pressure between bubbles and droplets will be higher. Conversely, it has been reported that ADV requires more acoustic power to trigger the vaporization of smaller the NDs. Targeted NBs have been proposed to improve tumor detection, since they share some of the advantages of NDs. However, their limited reflectivity at clinical frequencies remains an issue. By chasing targeted NBs or small MBs with NDs, bubbles will expand, thus enhancing their ultrasound signal and improving the detection of the targeted diseased tissue. The inventors validated this first milestone in vivo, using 1 µm rhodamine-labeled MBs that target MC38 cancer cells in a tumor-bearing mouse.

Nanobubbles Inflate when in Contact with Nanodroplets

Figure 24:
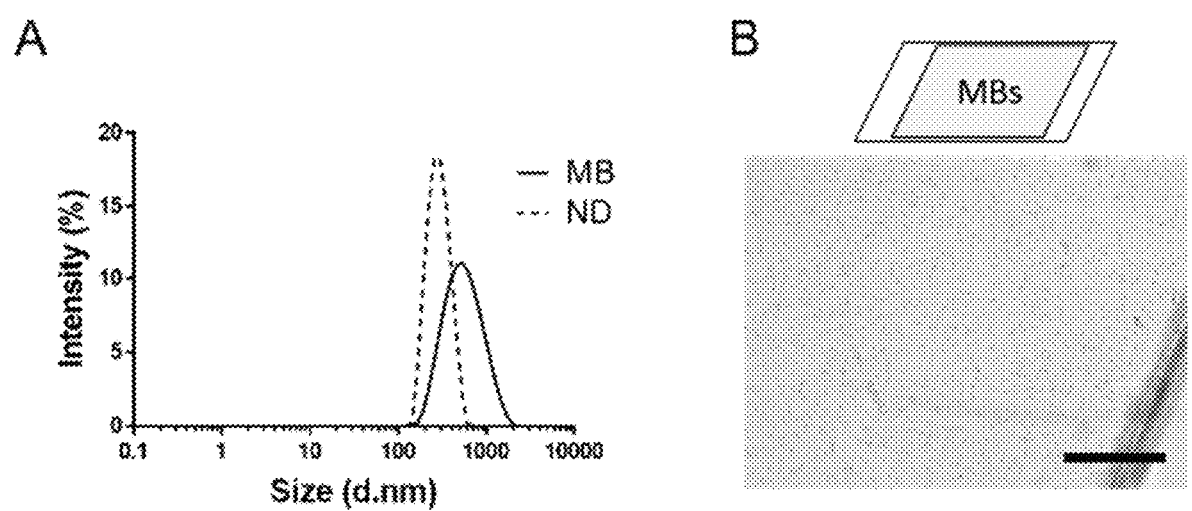
FIG. 24 illustrates shows representative ND and sub-micron MBsize distribution and representative bright field microscopy image of sub-micron MBs before the addition of NDs.
Figure 27:
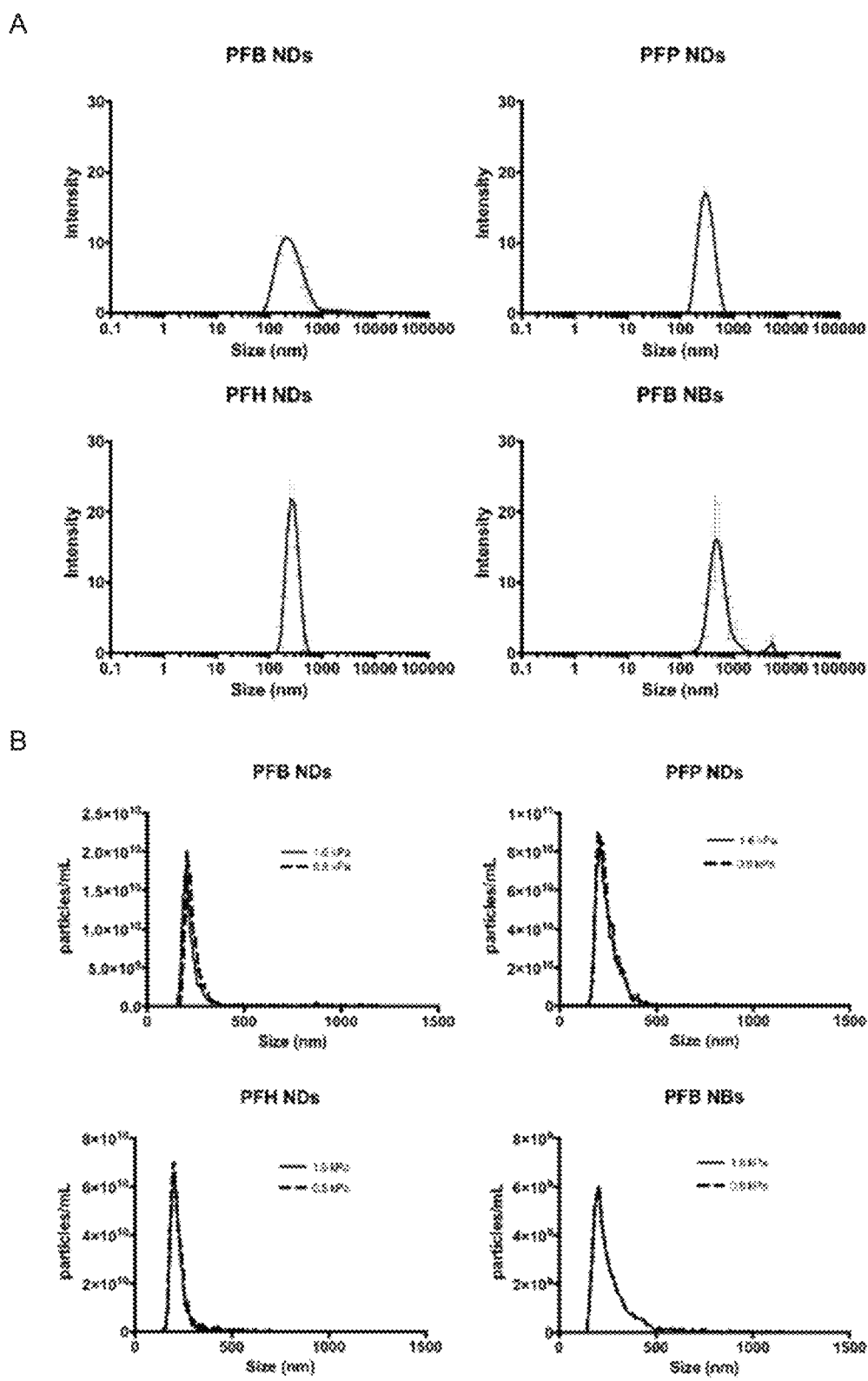
FIG. 27 shows representative ND and NB size distribution measured by DLS and qNano Gold Tunable Resistive Pulse Sensing counter system.
Figure 29:
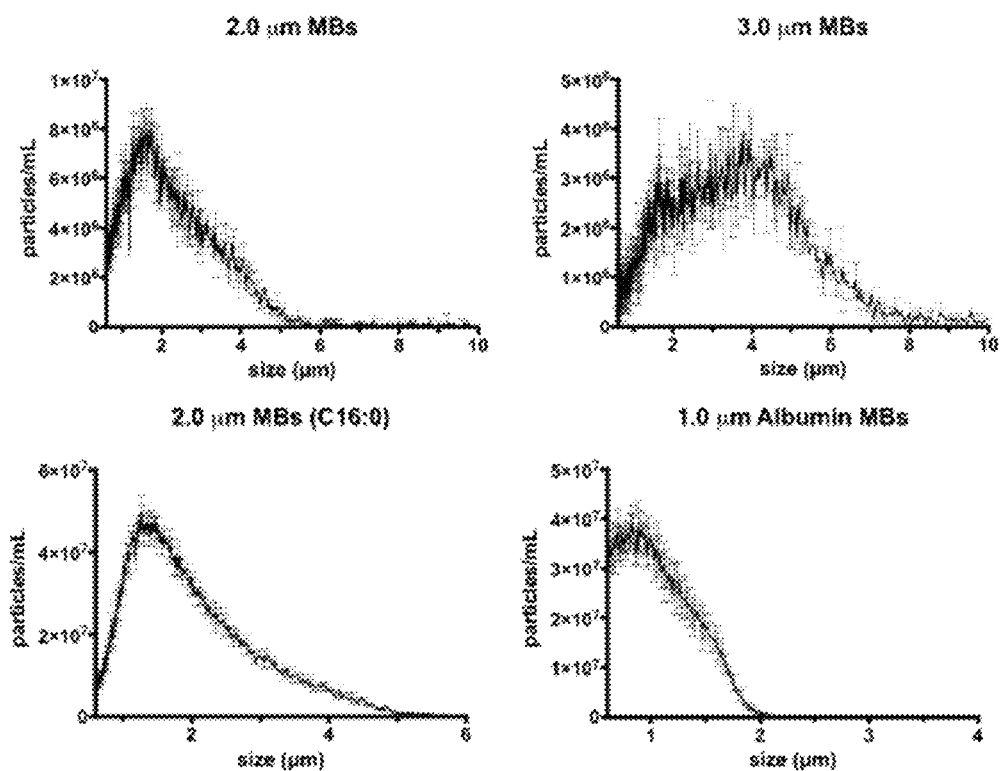
FIG. 29 shows representative MBsize distribution measured by a Multisizer 4 Coulter counter system.

As a proof of concept, the inventors first used perfluorobutane (PFB) nanobubbles (NBs) instead of regular microbubbles (>1 µm) to explore the effect of the addition of PFB NDs on the signal intensity by ultrasound imaging. NBs constitute a good model because of their limited US signal on B-mode imaging when exposed to low acoustic power. Both NBs and NDs were prepared with a phospholipid mixture composed of 1,2-Distearoylphosphatidyletha-nolamine (DSPC) and Distearoylphosphatidylethanolamine conjugated with polyethylene glycol 2000 (DSPE-PEG 2K) in a 90:10 molar ratio. Their hydrodynamic sizes were characterized by dynamic light scattering (DLS, Figure S1A) and were on average 488.1±4.6 nm and 285.2±0.9 nm with polydispersity indexes (PdI) of 0.20±0.004 and 0.17±0.003 for NBs and NDs respectively. Tunable resistive pulse sensing (TRPS) was used to measure their size and concentration (FIGS. 29 and 30). FIG. 24 shows (A) Representative ND and sub-micron MB size distribution measured by DLS. (B) Representative bright field microscopy image of sub-micron MBs before the addition of NDs. Scale bar=100 µm. FIG. 27 shows representative DLS (A) and TRPS (B) traces of nanodroplets and nanobubbles (n=3). FIG. 29 shows multisizer coulter counter traces of MBs (n=3).

Figure 11:
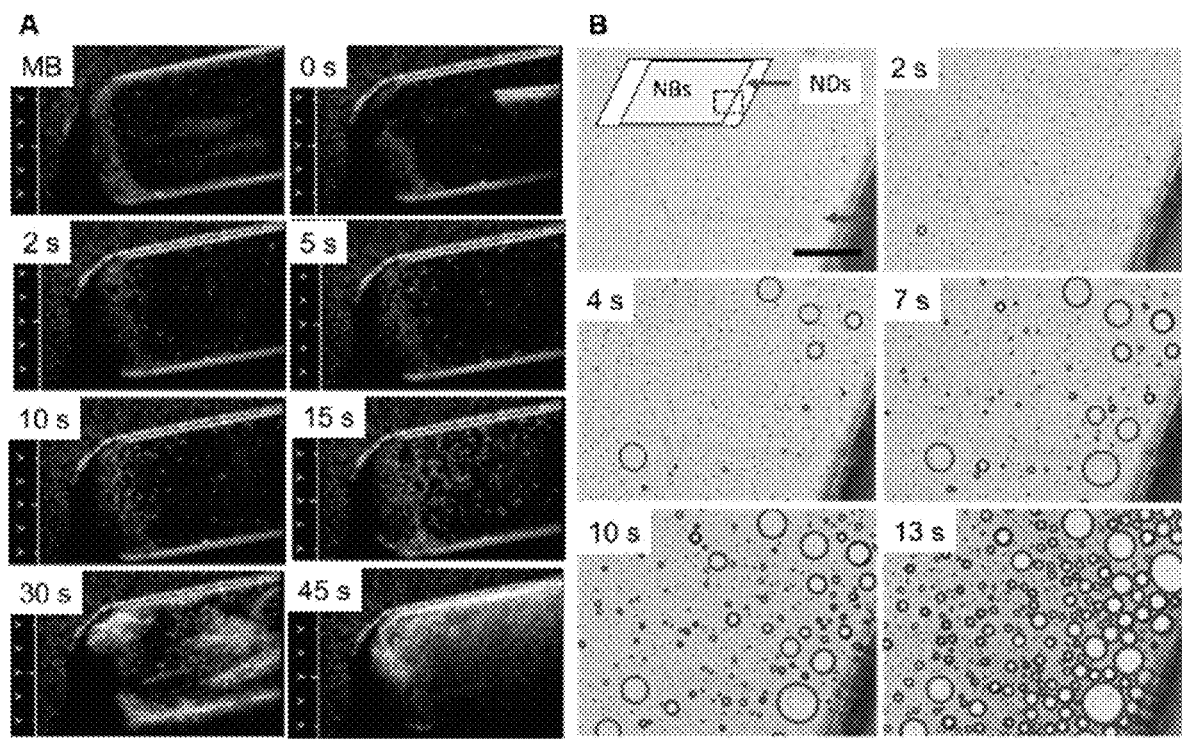
FIG. 11 illustrates PFB nanobubbles inflation triggered by the addition of PFB nanodroplets.
Figure 26:
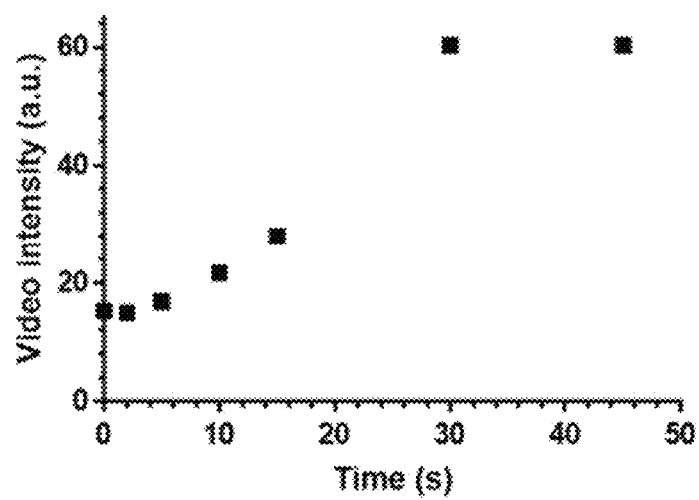
FIG. 26 illustrates graphical results of video intensity versus time for a suspension of NBs was prepared in PBS.

A suspension of NBs was prepared in PBS 1× ($3 \times 10^9$ NBs/mL) and introduced at the bottom of a plastic bulb with the intent of observing any change in buoyancy and echogenicity. The plastic bulb was then immersed in a water bath at 37° C. and imaged using B-mode imaging. US imaging at low mechanical index (MI=0.05) produced only a weak signal despite high concentration of NBs (FIG. 11A). Once the temperature of the NB suspension reached 37° C., a suspension of NDs in PBS 1× ($10^9$ NDs/mL) was added in the plastic bulb. After a few seconds, the ultrasound signal increased along with the appearance of numerous echogenic and buoyant MBs that started to rise to the surface. Regions of interest (ROIs) were drawn and the ultrasound video signal intensity in the plastic bulb was measured and resulted in a 4-fold enhancement after only 30 s post-ND addition (FIG. 24A and FIG. 26). Interestingly, the portion of the bulb located in the far field is not visible after 45 s, due to the acoustic shadowing that resulted from the high number of MBs formed by this inflation process. As expected (29), NDs alone did not produce any US signal when observed at low MI for 5 minutes (FIG. S4) and vaporized only when subjected to a MI=0.5. NB inflation was also observed optically by microscopy using the same samples used in the ultrasound experiment. Briefly, a small volume (10 µL) of NBs in PBS 1× ($1 \times 10^{11}$ NBs/mL) was first placed on a microscopy slide and covered with a coverslip and a small volume of NDs (10 µL) in PBS 1× ($1 \times 10^{11}$ NBs/mL) was then added between the slide and the coverslip to mix NBs and NDs together. The mixture was observed using bright filed microscopy at a 20× magnification. The first large MB was formed after only 2 seconds and more inflated MBs were formed subsequently with sizes above 50 µm (FIG. 11B). FIG. 11 illustrates PFB nanobubbles inflation triggered by the addition of PFB nanodroplets. A) B-mode ultrasound imaging of NBs before, immediately after, and 2, 5, 10, 15, 30 and 45 s after ND addition in PBS 1× at 37° C. B) Bright-field microscopy time lapse of NB inflation after ND addition. Scale bar is 100 µm Microbubbles Inflate without Contact with Nanodroplets While the two previous experiments provided evidence of inflation when NBs and NDs are mixed together in solution, they did not demonstrate if direct contact between NB and ND is necessary to trigger expansion. In addition, as both systems are in equilibrium with ambient pressure, the large expanded MBs have the ability to draw more air into them from outside and expand even more. The inventors expect that similar MB inflation will happen in plasma with the dissolved air.

Figure 12:
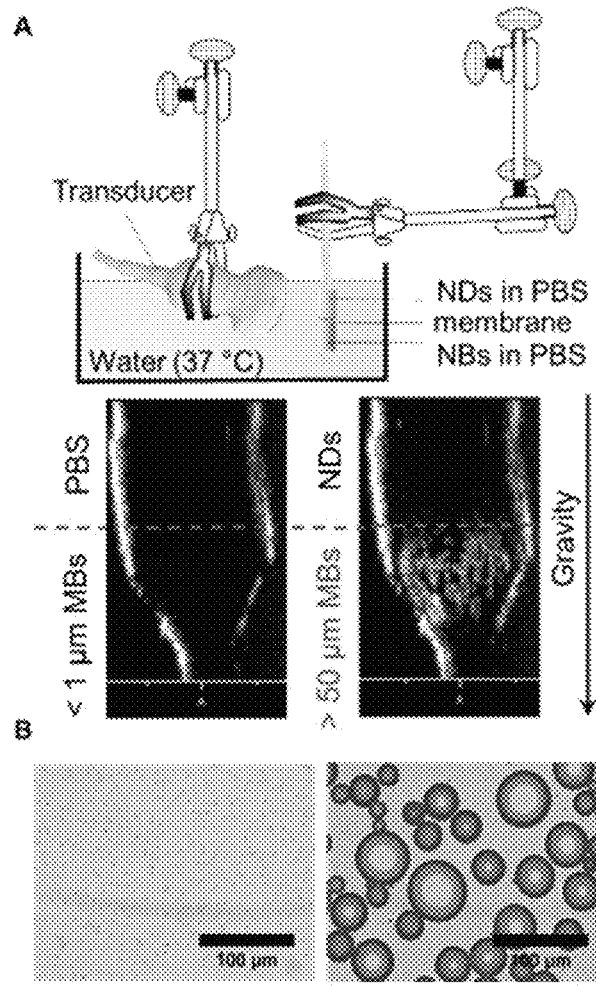
FIG. 12 illustrates an experimental setup and bright-field microscopy images showing a large amount of expanded MBs.

To assess if direct contact is necessary to trigger inflation, the inventors performed two additional experiments using ultrasound imaging and microscopy. In a first experiment, two soft plastic bulbs halves were attached to each other, their inner compartments separated with a semi-permeable dialysis membrane (3.5 kDa molecular weight cutoff, 60 µm thickness). The lower compartment was filled with a suspension of PFB NBs in PBS 1×, while the upper compartment was first filled with PBS 1×. The two-compartment sample holder was then placed in a water bath at 37° C. and was imaged by ultrasound at low MI (MI=0.05) (FIG. 12A). A suspension of PFB NDs was then added in the upper compartment. The semi-permeable membrane allows small molecules such as PFB or phospholipids to freely diffuse while preventing NDs and NBs from diffusing from one compartment to the other. Using on B-mode imaging at 8 MHz, no signal was visible in the lower compartment containing NBs. Interestingly, less than 1 min after the addition of NDs in the upper compartment, a significant ultrasound signal was observed in the lower compartment, characteristic of echogenic microbubbles being inflated. (FIG. 12A). Samples before and after addition of NDs were collected and observed under the microscope to visually assess NB expansion. Bright-field microscopy showed a large amount of expanded MBs with many around 50 µm in size (FIG. 12B). FIG. 12 shows validation of MB expansion in the presence of NDs without direct contact using ultrasound imaging and optical microscopy. A) Schematic representation of the ultrasound setup using two compartments separated by a semi-permeable membrane and B-mode US imaging before (left) and after (right) the addition of NDs in the upper compartment. B) Representative bright-field microscopy images of NBs in the lower compartment before (left) and after (right) addition of NDs in the upper compartment.

Figure 13:
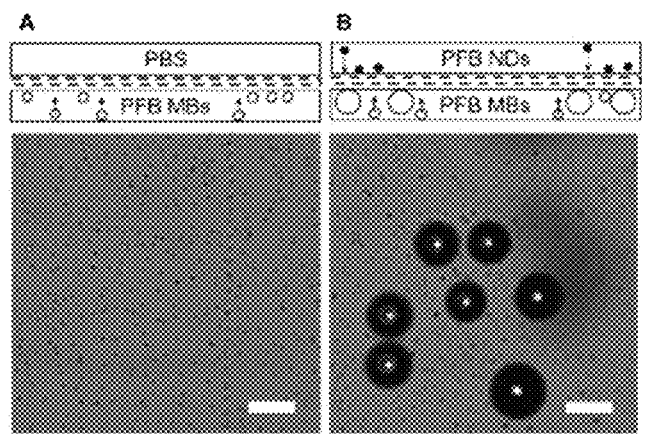
FIG. 13 illustrates an optically transparent two-compartment system separated by a semi-permeable membrane between a microscopy slide and a coverslip to observe MB inflation in real time using bright-field microscopy.

In a second experiment, an optically transparent two-compartment system separated by a semi-permeable membrane (MWCO=3.5 kDa, 60 µm thickness) was built between a microscopy slide and a coverslip to observe MB inflation in real time using bright-field microscopy (FIG. 13A). A MB suspension in PBS 1× was placed in the lower compartment and either PBS 1× or a suspension of NDs in PBS 1× were added in the upper compartment. The focal plane was adjusted to observe MBs in the lower compartment during the addition of PBS 1× or NDs in the upper compartment. As expected, no expansion was observed when PBS 1× was added while the formation of 50 µm inflated MBs was observed when NDs were added after around 5 minutes (FIG. 13B). FIG. 13 illustrates an observation of MB expansion in the presence of NDs without direct contact using microscopy. Top: Schematic representation of the two-compartment system containing MBs in the lower compartment and either PBS 1× (A) or NDs (B) in the upper compartment. Bottom: Representative bright field images of MBs in the lower compartment after addition of PBS (A) or NDs (B) in the upper compartment. Scale bar is 100 µm.

Membrane Fusion Occurs Between NDs and MBs During Inflation.

To assess if any membrane fusion occurs during the inflation process, NDs and MBs formulated using phospholipids labeled with Cy5.5 (Cy5.5-MBs) or fluorescein (Fl-NDs) respectively. Flow cytometry was then used to evaluate the fluorescence of the MBs after addition of Fl-NDs (FIG. 5A). ROIs P3 and P4 were drawn on the scatter-plots to identify NDs and MBs respectively. Gating the MBs (P4 gate), a bivariate histogram was generated with four quadrants for the four possible fluorescence combinations (Fl−/Cy5.5−, Fl+/Cy5.5−, Fl−/Cy5.5+, Fl+/Cy5.5+). While MBs were initially Fl−/Cy5.5+ in the lower right quadrant (99.8% in Q4-LR), the addition of Fl-NDs caused a shift of the MB signal to the Fl+/Cy5.5+ upper right quadrant within a minute (97.7% in Q4-UR), which indicates that Fl-labeled phospholipids from NDs were incorporated into the MB phospholipid shell, thus demonstrating membrane fusion. Finally, a P4-gated histogram representing the particle count in function of forward scatter (FSC) demonstrated MB expansion as 81.3% of the inflated MBs were bigger than the largest MBs prior to ND addition.

Figure 25:
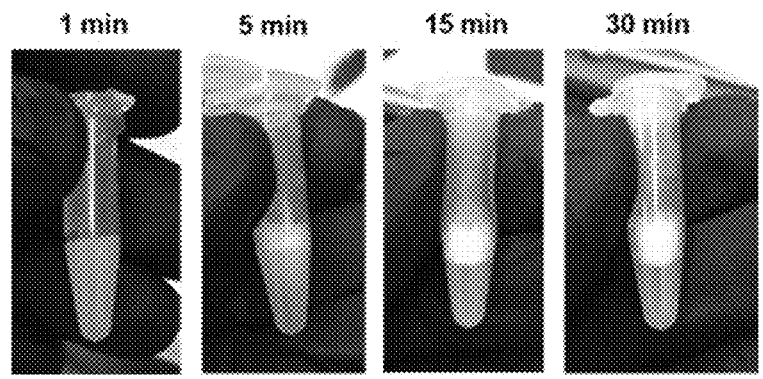
FIG. 25 illustrates representative pictures of ND-MB mixtures at different time intervals.

As MBs kept inflating overtime (FIG. 25), larger MBs started to accumulate to the surface over time to form a foamy upper layer. In addition, as these expanded MBs are saturated in PFC and the sample is in equilibrium with ambient pressure, expanded MBs most likely pulled air from the surface to expand even more. Because of their extreme buoyancy, the number of inflated MBs is underestimated by flow cytometry, as a large population of inflated MBs is not injected in the flow cytometer since its inlet is located at the bottom of the sample tube. In addition, MBs>40 µm are not detected as they are above the detection limit of the instrument. Because of these limitations, the quantitative analysis of the expansion of MB with ND was not possible using flow cytometry. FIG. 25 shows representative pictures of the ND-MB mixtures. The foam observed on top of the Eppendorf are characteristics of large buoyant MBs that float to the top.

To confirm the flow cytometry data, the inventors also used fluorescence microscopy to visualize membrane fusion by observing the incorporation of lipids from the NDs shell in the inflated MBshell. In a first microscopy experiment, the inventors labeled the phospholipid membranes of MBs and NDs with the lipophilic tracers DiD (1,1′-dioctadecyl-3,3,3′,3′-tetramethylindodicarbocyanine) and DiO (3,3′-dioctadecyloxacarbocyanine) respectively. Addition of DiO-labeled NDs in a suspension of DiD-labeled MBs lead to the formation of inflated MBs exhibiting both DiO and DiD fluorescence (FIG. 5B), providing further evidence of a membrane fusion phenomenon.

Figure 14:
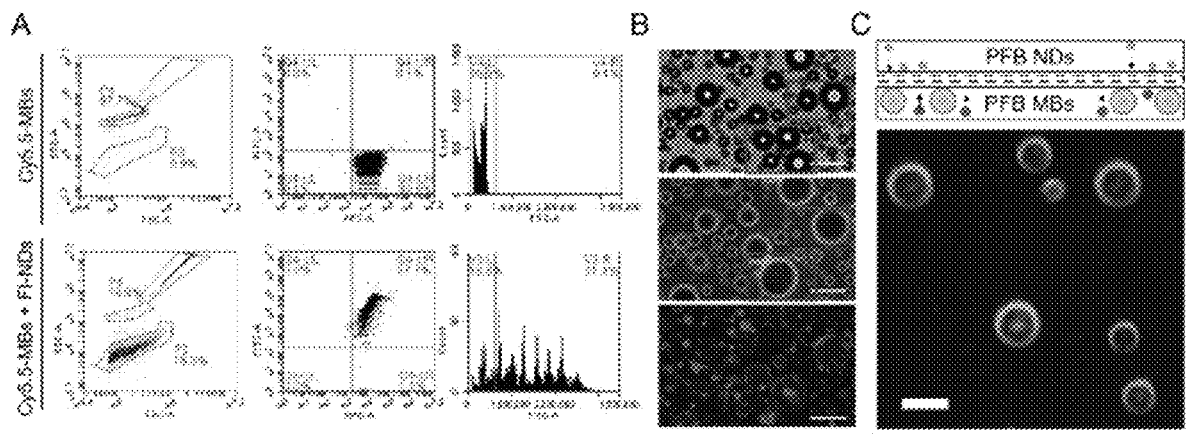
FIG. 14 Sections A and B illustrate that both lipophilic payload and phospholipid shell transfer during MB inflation, using microscopy and flow cytometry. Section C illustrates an experimental setup equivalent to that of FIG. 13 using fluorescently labeled MBs and NDs.

To provide further insight in the inflation mechanism, an experimental setup identical to that described for FIG. 13 was employed but using Cy5.5-MBs and Fl-NDs at similar concentrations. Surprisingly, while NDs and MBs were separated by a 60 µm thickness membrane with MWCO of 3.5 kDa, the inventors found that DSPE-PEG2K-fluorescein (MW=2.4 kDa) were incorporated in the inflated shell of the MBs within minutes (FIG. 14C). These results suggest that expanded MBs formed with our process will be most likely more stable than MBs generated from ADV. FIG. 14 shows a demonstration of membrane fusion between NDs and MBs during inflation. A) Flow cytometry data of Cy5.5-MBs alone (top) and Cy5.5-MBs mixed with Fl-NDs (bottom) including a scatter-plot (left) with ROIs drawn for MBs (P4) and NDs (P3), a P4-gated bivariate histogram (center) with four quadrants for the four possible fluorescence combinations (Fl−/Cy5.5−, Fl+/Cy5.5−, Fl−/Cy5.5+, Fl+/Cy5.5+), and P4-gated particle count in function of forward scatter (higher forward scatter=larger size). B) Representative bright field and fluorescence microscopy images showing colocalization of DiO-NDs and DiD-MBs. Red boxes highlight coalescence and fusion of MBs observed between acquisitions of bright field and fluorescence images. C) Validation of fluorescein labeled phospholipid transfer through the dialysis membrane (3.5 kDa cutoff, 60 µm thickness). top) Schematic representation of the two-compartment system with Fl-NDs and Cy5.5-MBs. bottom) Representative bright field image of inflated MBs in the lower compartment that now contains Fl-DSPE-PEG. Scale bar is 100 µm.

Figure 15:
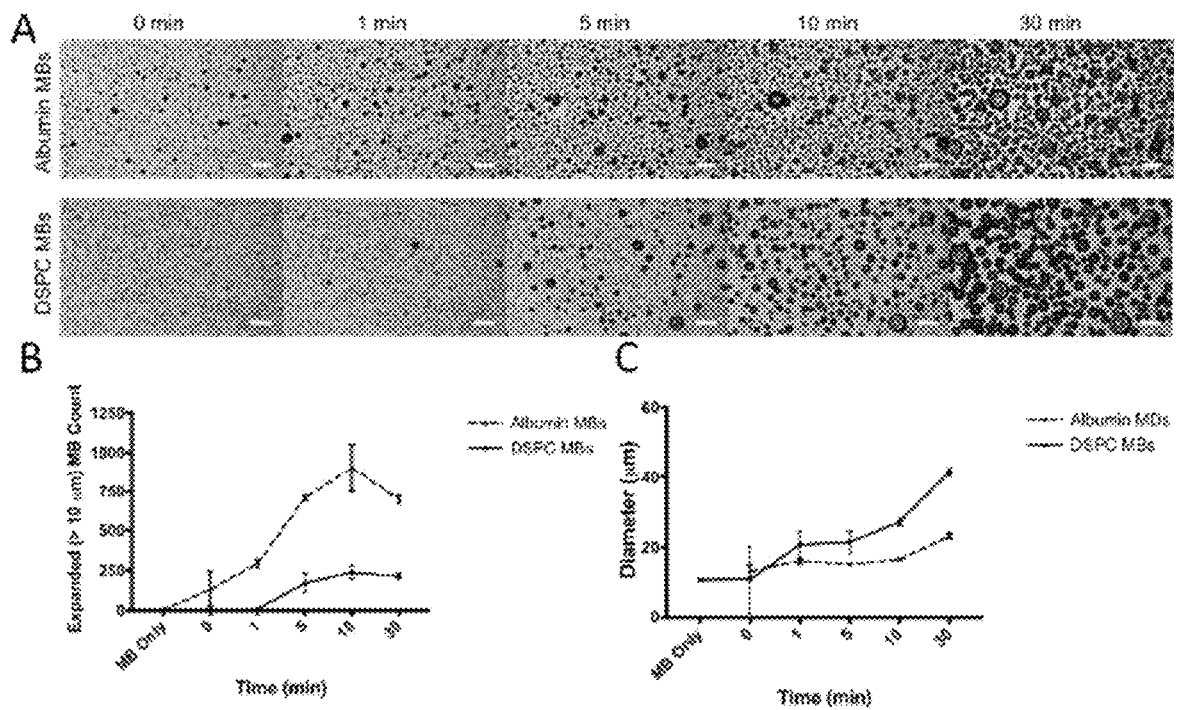
FIG. 15 illustrates the different inflation kinetics between albumin-MBs and phospholipid based MBs.

To assess whether a phospholipid membrane was needed to induce MB inflation, the inventors also investigated the ability of MBs with a shell composed of denatured albumin to expand when in contact with phospholipid based NDs. Albumin-based MBs are formulated by tip sonication of albumin in the presence of PFB. The heat generated by sonication denatures and crosslinks albumin via disulfide bonds to form a stiff shell around the PFC core. The inventors hypothesized that a polymer-based or crosslinked proteins shell may physically limit bubbles' growth, as lipid surfactants provided by NDs should not contribute and promote further inflation. To observe MB inflation in real time, the inventors place a suspension of albumin-MBs in a hemocytometer plate and added a suspension of PFB-NDs. Interestingly, albumin-MBs inflated at a fast rate, exhibiting MBs>10 µm immediately after addition of PFB phospholipid NDs (FIG. 15A, B). However, the maximal size reached by inflated albumin-MBs was limited to an average of 23±x µm 30 minutes after ND addition (FIG. 15C), which is smaller than sizes observed in our previous experiments with phospholipid-based MBs. This experiment further validated our hypothesis that PFC transfer occurs without membrane fusion and despite the different shell compositions between NDs and MBs. FIG. 15 shows inflation occurs when Albumin MBs are mixed with phospholipid PFB NDs. (A) Bright-field microscopy images of albumin MBs over time. B) Number and C) average size of inflated albumin-MBs over time. Scale bar is 100 µm.

Lower Molecular Weight PFCs in ND Core Induce Higher Count and Faster MB Inflation.

Figure 16:
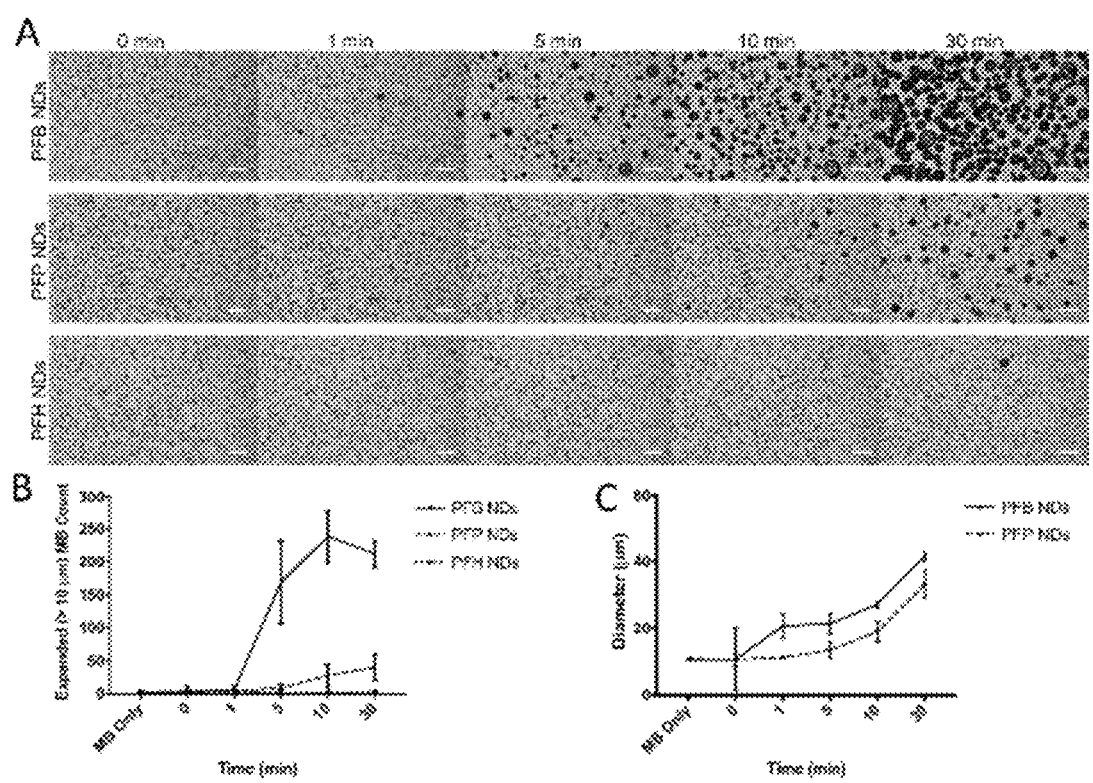
FIG. 16 includes bright-field microscopy and graphical images showing the effect of ND PFC core on PFB MBs inflation.

Nanodroplets described herein were formulated by microfluidization using either PFB, perfluoropentane (PFP) or perfluorohexane (PFH) as liquid core with phospholipid shells containing DSPC and DSPE-PEG2K with a 90:10 molar ratio. PFB MBs were prepared with the same phospholipid compositions so they all share the same interfacial tension. All ND samples were characterized by DLS and their hydrodynamic diameters were on average 221±4 nm (PFB), 295±1 nm (PFP), and 268±5 nm (PFH) (FIG. 28). ND size and concentration were measured using TRPS (FIG. 27 and FIG. 28). Both DLS and TRPS data confirmed that the ND size was not affected by the nature of the encapsulated PFC, which was expected as microfluidization using high shear fluid processors is an efficient technique to reduce and achieve uniform emulsion size. PFB NDs yielded the largest amount of inflated MBs and exhibited the highest inflation rate. PFP ND yielded some inflation after 10 min and inflated MBs to a lesser extent with no MB>40 µm. Finally, PFH NDs did not yield any MB inflation. This result validated our hypothesis that lower molecular weight PFC are transferred more efficiently into MBs, most likely as a result of their lower intermolecular cohesiveness, higher PFC vapor pressure (PFB: 330.0 kPa, PFP: 84.0 kPa, PFH: 31.0 kPa) and volatility (30). FIG. 16 shows the effect of ND PFC core on PFB MBs inflation. A) Representative bright-field microscopy images showing MB inflation after the addition of perfluorobutane (PFB), perfluoropentane (PFP), or perfluorohexane (PFH) NDs (scale bar=100 µm). B) Number and C) average size of inflated MBs over time.

Large MBs Inflate Faster than Small MBs or NBs.

Figure 17:
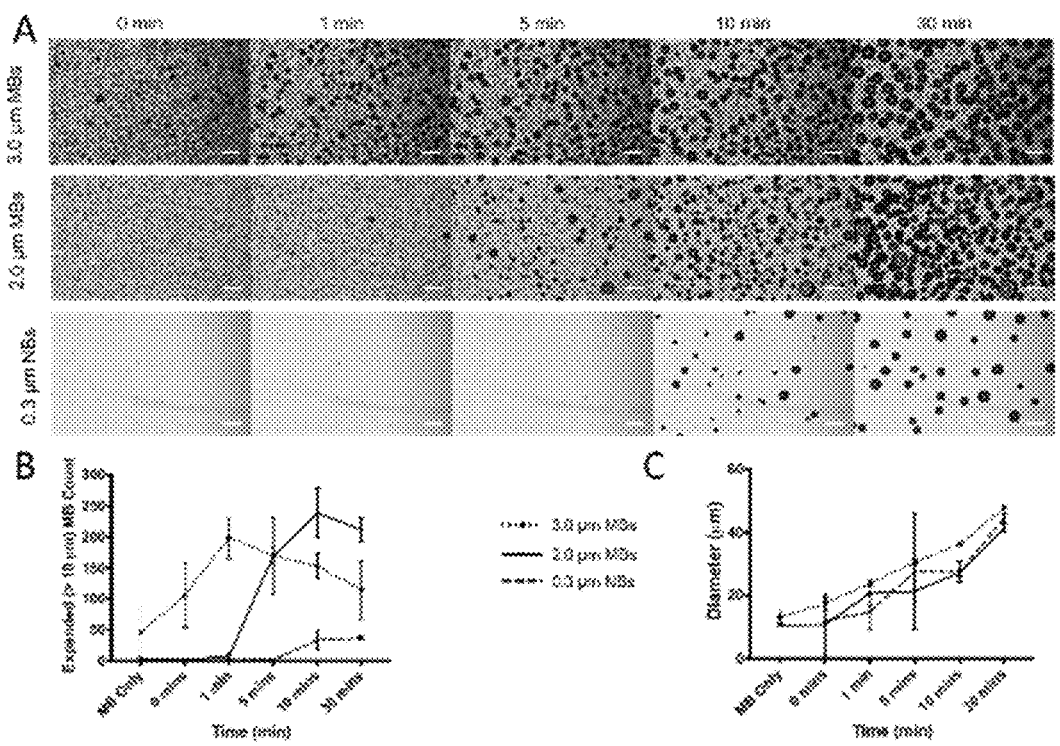
FIG. 17 includes bright-field microscopy and graphical images showing the effect of bubble size on inflation.

The inventors' hypothesis is that the larger MBs will be inflated at a faster rate compared to smaller MBs or NB due to the greater difference in Laplace pressure in regard to NDs (assuming equal interfacial tension). For these reasons, the inventors tested the inflation rate of bubbles with different mean sizes (3 µm, 2 µm, and 0.3 µm) when combined with NDs at a ND/MB ratio of 100:1. Both droplets and bubbles were formulated with the same phospholipid shell composition (DSPC:DSPE-PEG2K at a 90:10 molar ratio). When mixed with NDs, the larger 3 µm MBs started to expand immediately after ND addition, while 2 µm MBs and 0.3 µm NBs started to inflate 5 and 10 min after ND addition respectively (FIG. 17A). Assuming equal surface tension, 3-µm MBs are under lower interfacial tension than 2-µm MBs and 0.3-µm NBs. According to Laplace law, the inventors hypothesize that as liquid PFC in NDs exhibit a much higher interfacial pressure difference with big MBs, PFC transfer will happen faster with 3-µm compared to 3-µm and 0.3-µm MBs. In addition, the inventors assume that, at similar NDs to MBs ratio, the opportunity for the NDs to interact with NBs and transfer its PFC and phospholipids is lower due to a decreased probability to be close to each other. Interestingly, both NBs and MBs continued to inflate over 30 min reaching nearly similar size. This is in agreement with the inventors' theory that the large vapor pressure in the NDs is the main driving force, as the concentration gradient is expected to be the same whatever the bubble size. FIG. 17 shows the effect of bubble size on their inflation. A) Representative bright-field microscopy images showing inflation of 3 µm, 2 µm and 0.3 µm MBs after the addition of PFB NDs at a 100:1 ND/MB ratio (scale bar=100 µm). B) Number and C) average size of inflated MBs over time.

Figure 18:
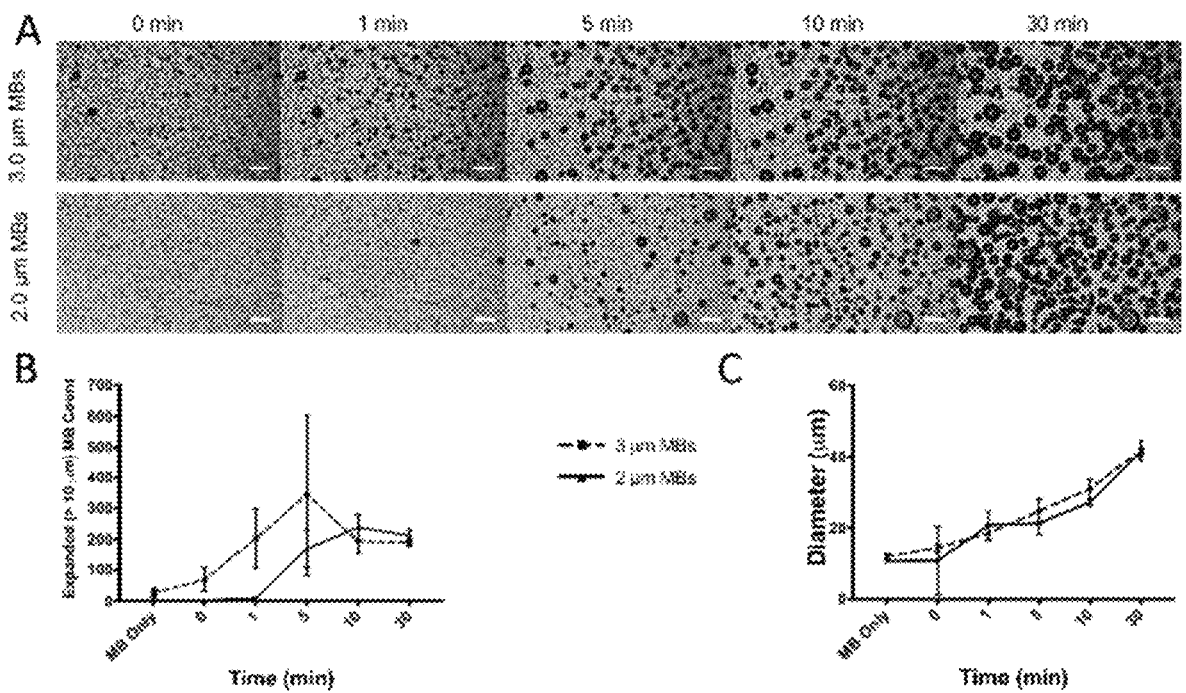
FIG. 18 includes bright-field microscopy and graphical images showing the effect of bubble size on inflation for 2 µm and 3 µm MBs while keeping the PFB volume ratios between NDs and MBs constant.

In order to better compare the effect of MB size on inflation, the inventors also compared the inflation of 2 µm and 3 µm MBs while keeping the PFB volume ratios between NDs and MBs constant, as opposed to keeping a 100:1 NB/MB concentration ratio. This experiment exhibited a similar trend compared to the previous experiment with larger 3 µm MBs being inflated at a faster rate than 2 µm MBs (FIG. 18). FIG. 18 shows MB inflation of 2 µm and 3 µm MBs while keeping PFC volume ratio between ND and MB constant. A) Representative bright-field microscopy images of inflation over time. B) Number and C) average size of inflated MBs over time. Scale bar is 100 µm.

MB and ND Membrane Compositions Dictates MB Inflation Kinetics.

Figure 19:
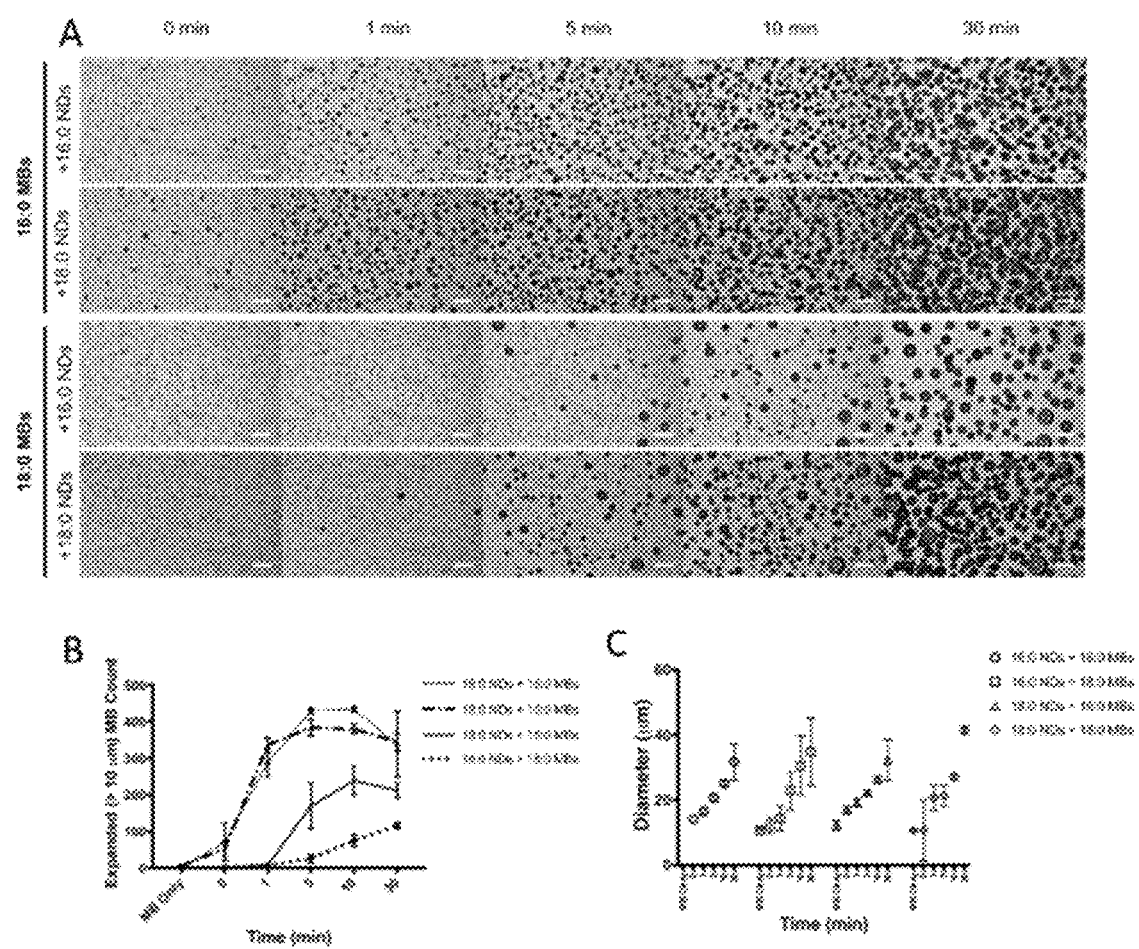
FIG. 19 includes bright-field microscopy and graphical images showing the effect on phospholipid acyl chain length on MB inflation.

It is known that the transition temperature of phospholipids increases with the acyl chain length. This causes MBs formulated using phospholipids with longer acyl chains to have more cohesive shells. This increase in shell cohesiveness should delay the transfer of PFC gas across the MB membrane due to the increase in attractive hydrophobic and van der Waals interactions between the adjacent phospholipids' hydrophobic tails. For these reasons, the inventors performed a series of experiments to explore the impact of the intermolecular forces between phospholipids in MB and ND shell on MB inflation. Specifically, the inventors compared the rate and extent of inflation using MBs and NDs made from DSPC (18 carbons in each acyl chain and 0 insaturation, 18:0) or 1,2-dipalmitoyl-sn-glycero-3-phosphocholine (DPPC, 16:0). All MB/ND combinations were tested at a 100:1 ND/MB ratio. The inventors selected these two phospholipids because while they are both common MB constituents, they are in two different lipid physical state at 37° C., either in their ordered gel phase (lipid chains extended and closely packed) or fluid phase (lipid chains randomly organized) for 18:0 and 16:0 respectively. As expected, MBs made with 16:0 phospholipids underwent a faster and more important inflation than their analogues with 18:0 phospholipids, and so with NDs composed of either 18:0 or 16:0 phospholipids (FIG. 19). This result is most likely due to the easier gas penetration through the monolayer composed of phospholipids with shorter acyl chains (32).

While less lipid intermolecular cohesion forces in NDs made of 16:0 vs. 18:0 phospholipids are known to result in lower activation energy needed to acoustically trigger ND vaporization (33), our results showed 18:0 MBs inflated to a greater extent with 18:0 NDs as opposed to 16:0 NDs. While the inventors do not have an indisputable explanation, the inventors hypothesize that the fact that 18:0 NDs were smaller than their 16:0 counterpart compensated their lower interfacial tension resulting in similar or close Laplace overpressure. This result may also be explained by the presence or absence of surface microstructures that have been reported in MBs composed of DSPC and DPPC respectively (34). The inventors hypothesize that similarly to MBs, 18:0 NDs have surface microstructures whereas 16:0 NDs do not, which explain their more favorable phospholipids and gas transfer. FIG. 19 shows the effect on phospholipid acyl chain length on MB inflation. A) Representative bright-field microscopy images of MB inflation using MBs/NDs with 18:0 (DSPC) and 16:0 (DPPC) phospholipids lengths (scale bar=100 μm). B) Number and C) average size of inflated MBs over time.

Targeting NDs to MBs Through Bioorthogonal Click Chemistry Facilitates MB Inflation.

Figure 20:
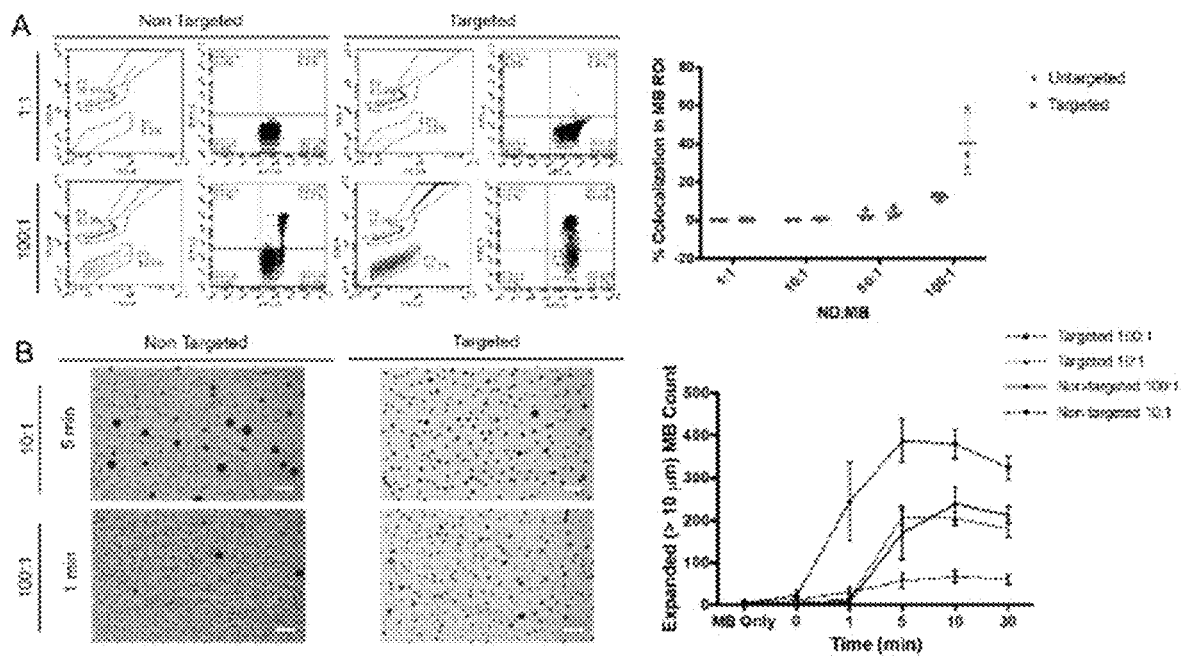
FIG. 20 includes bright-field microscopy and graphical images demonstrating the impact of ND/MB targeting in the inflation level using Non Targeted (Cy5.5-MBs+Fl-NDs) and Targeted (Cy5.5-DBCO-MBs+Fl-Azide-NDs) particles.

To prove the effect of targeting on non-acoustic droplet vaporization, the inventors used bio-orthogonal click chemistry, a copper-free click chemistry reaction between an azide and a strained alkyne (e.g., cyclooctyne) that has been used in vivo for imaging (35, 36) or therapy (37) with no toxicity. The inventors expect that targeting NDs to MBs will bring them into close proximity to ease PFC transfer, increase lipid fusion, and maximize inflation while minimizing dose. The inventors used dibenzocyclooctyne (DBCO) as our strained alkyne, because it is commercially available already attached to a PEGylated phospholipid and has been shown to trigger artificial membrane fusion with azide-labeled phospholipids.(38) To demonstrate the advantage of targeting NDs to MBs, the inventors tested a series of ND:MB concentration ratios (1:1 to 100:1) while keeping the MB count and volume constant. MB inflation was assessed by flow cytometry as described above, using Cy5.5-MBs and Fl-NDs (Non targeted) as well as Cy5.5-DBCO-MBs and Fl-Azide-NDs. Below 100:1 ND: MB ratio, the inventors did not observe any MB inflation with or without targeting at the concentrations tested. However, at a 100:1 ND:MB ratio, while only 12.1±2.1% MBs inflated in the non-targeted samples, 40.2±16.4% DBCO-MBs inflated (FIG. 20A). The inventors hypothesized that non-targeted ND most likely did not interact with non-targeted MBs as much as they targeted analogues which resulted in a lower inflated MB count. Even if the previous experiment described above were in agreement with an effect of targeting on MB inflation, the inventors believe that this effect is underestimated due to the flow cytometry limitation mentioned earlier. To provide further evidence of the enhanced MB inflation when MB and ND are targeted to each other's, the inventors evaluated by microscopy MB inflation in the presence of NDs using disposable hemocytometers (FIG. 20B). Contrary to the flow cytometer, this microscopy study does not suffer from MB buoyancy or increased size. FIG. 20 shows a demonstration of the impact of ND/MB targeting in the inflation level using Non-Targeted (Cy5.5-MBs+Fl-NDs) and Targeted (Cy5.5-DBCO-MBs+Fl-Azide-NDs) particles. A) Left: Flow cytometry scatter-plots with ROIs drawn for MBs (P4) and NDs (P3), and P4-gated bivariate histograms with four quadrants for the four possible fluorescence combinations (Fl−/Cy5.5−, Fl+/Cy5.5−, Fl−/Cy5.5+, Fl+/Cy5.5+) of Non Targeted (left) and Targeted (right) at 100:1 (bottom) and 1:1 (top) concentration ratios. A) Right: Percentage colocalization between Non-Targeted and Targeted at P4-gated bivariate histogram in the upper right quadrant (Fl+/Cy5.5+) as a function of increasing ND:MB concentration ratios. B) Left: Representative bright-field microscopy images of MB inflation using Non targeted and Targeted MBs/NDs (scale bar=100 μm). B) Right: Number of inflated MBs over time.

Immobilized Microbubbles Inflate when in Contact to Nanodroplets in Flow Conditions in PBS 1× and in Blood.

Figure 21:
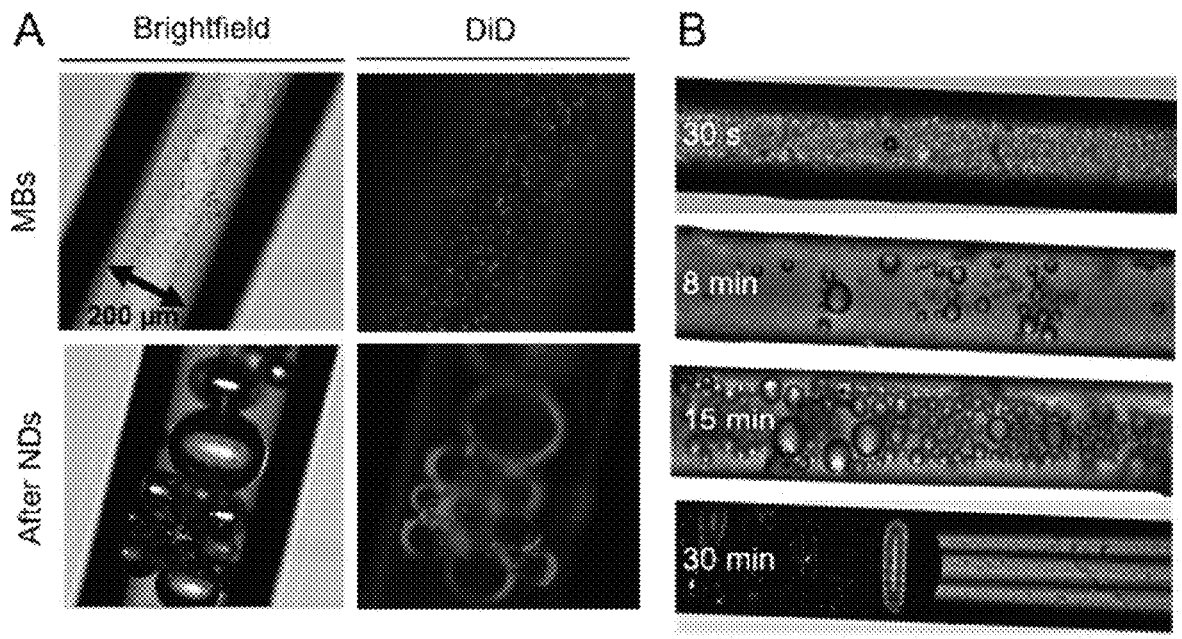
FIG. 21 includes images showing a vessel occlusion using an in vitro flow system in PBS 1× and in blood.

To evaluate the potential of the approach for in vivo applications, the inventors performed in vitro experiments in a flow system using PBS1× and whole blood. Since flow conditions will render interactions between ND and MB more challenging, the inventors assessed the effect of flow on MBs/NBs inflation in order to validate their formulations and inflation conditions prior to in vivo experiments. To mimic blood vessels and cell receptors, the inventors used a medical polyimide tubing (200 μm I.D.) coated with fluorescein. This coating was done by filling the tube with ethylenediamine and then conjugating the free amines with NHS-FITC using EDC as a coupling agent as previously reported (39). For the experiment in PBS1×, MBs were composed of DSPC, DSPE-PEG and DSPE-PEG-maleimide at a 90:8:2 molar ratio. NDs were composed of DSPC, DSPE-PEG, DSPE-PEG-Mal and DSPE-PEG-FITC with a 90:6:2:2 molar ratio. For the experiment in blood, lipid compositions were identical for both MBs and NDs but MBs. In order to mimic receptor targeting, MBs were conjugated with an anti-FITC antibody. Briefly, anti-FITC antibody was first thiolated using 2-iminothiolane, purified through a desalting column, and reacted with MBs via a thiol-ene coupling reaction. Targeted MBs ($10^7$/mL), in PBS 1× or in blood, were infused through the tube at a flow rate mimicking capillarity velocity (0.01 cm/s, 0.19 μL/min for 5 min) and then washed with PBS 1× or blood to remove unbound MBs (manual infusion). Bound MBs were easily visible after the wash in PBS but not in blood (FIG. 21A-top in PBS, data not shown in blood) by microscopy. Fluorescein-labeled NDs (Fl-NDs) were infused at the same flow rate. MB inflation and tube occlusion occurred within seconds after NDs infusion ($10^{10}$/mL) in PBS (FIG. 21A-bottom), with MB fusion observed in real time upon contact. In blood, the inventors observed a few MB inflated below a minute, however no coalescence was observed between inflated MBs until 15 min of ND infusion. Partial blood flow occlusion was observed after 15 min (red blood cell accumulation observed upstream from the occlusion site via darkening of the tube) and blood flow cessation was observed after 30 min (FIG. 21B). Note that after 30 min, a blood clot formed in the tube because of lack of flow. Blood flow was recovered by increasing the syringe pump volume dramatically (10 μL/min, >5.2 mm/s). This delayed onset of both inflation and fusion observed in blood was expected because of the higher blood viscosity that likely slightly decrease PFC gas kinetics transfer and stabilize inflated MBs towards coalescence. FIG. 21 shows a vessel occlusion using an in vitro flow system in PBS 1× and in blood. A) Representative bright field (left) and fluorescence (right) microscopy images of MBs before (top) and after (bottom) NDs infusion. B) Representative bright field of MBs during NDs infusion in blood.

In Vivo Validations of Microbubble Expansion.

Figure 22:
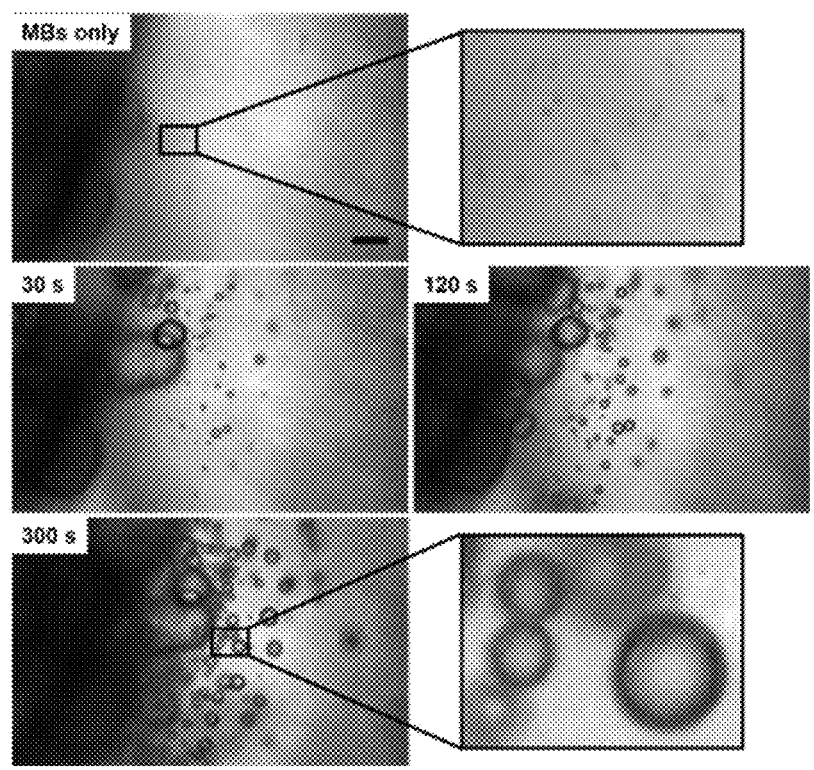
FIG. 22 illustrates a demonstration of MB inflation in vivo after subcutaneous NDs infusion.

The inventors first injected $10^6$ MBs diluted in 10 uL PBS into the subcutaneous space of a mouse skin flap to assess if MB inflation would occur in vivo. 5 min post MB injection (FIG. 22), $5\times10^9$ NDs diluted in 10 uL PBS were injected along the same tract into the subcutaneous space. While observing the injection area, the 1 μm MBs visualized in bright-field started to expand after 30 s post ND injection. The inventors were also able to observe both an increase in the number of expanded MBs, as well as continued expansion of already expanded MBs up to ~50 μm. FIG. 22 shows a demonstration of MB inflation in vivo after subcutaneous NDs infusion. Scale bar is 100 μm.

The inventors then injected $2\times10^8$ targeted MBs diluted in 100 uL PBS into the right retro-orbital sinus of a MC38-bearing nude mice to assess whether MB inflation would occur in vivo and in blood (FIG. 13). Targeted MBS were composed of DSPC, DSPE-PEG, DSPE-PEG-maleimide and 1,2-dipalmitoyl-sn-glycero-3-phosphoethanolamine-N-(lissamine rhodamine B sulfonyl) (DPPE-Liss Rhod) at an 89.5:5:5:0.5 molar ratio. In order to mimic receptor targeting, MBs were conjugated with an anti-phosphatidylserine (PS) antibodies. Antibodies targeting PS are one of the most selective strategies to target tumor blood vessels and have been validated in numerous animal models of cancer. After 15 min, the inventors proceeded to create a dorsal skin flap, as done previously with the tumor in the center of the viewing window (see FIG. 23A).

Figure 23:
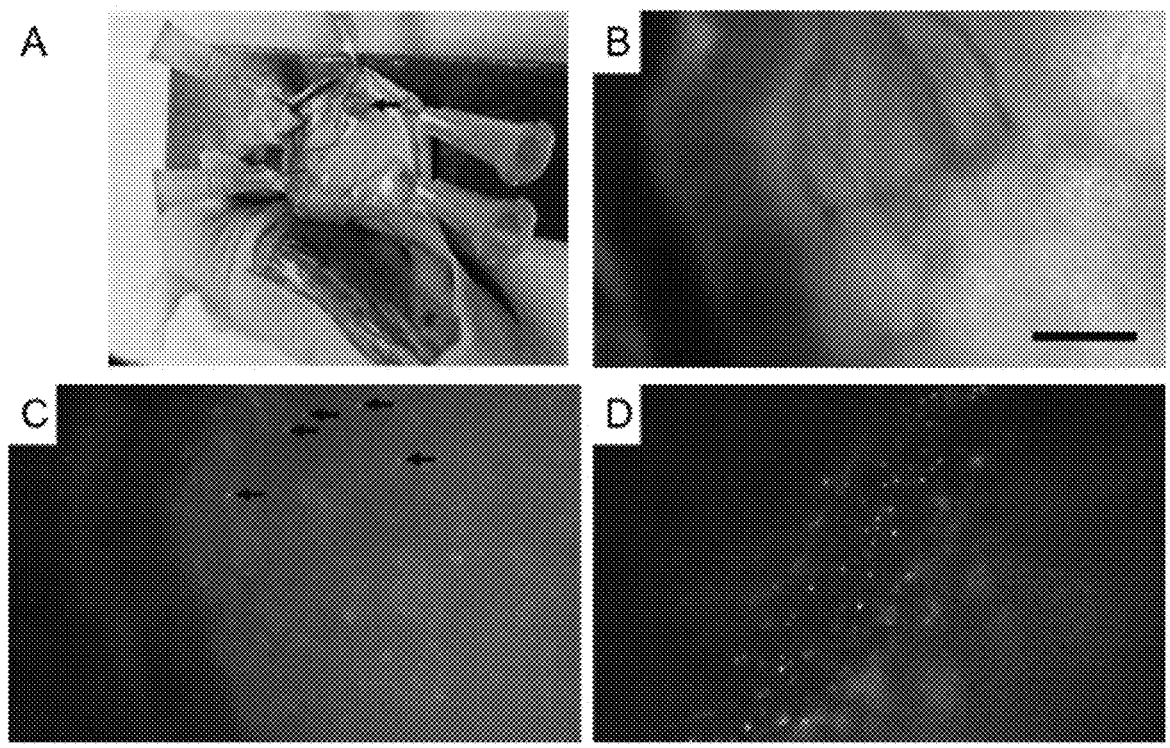
FIG. 23 illustrates a demonstration of MB targeting and inflation in vivo after intravenous NDs infusion.

Due to their small size (~1 μm) and most likely deep location within the attenuative tissue, MBs were not easily localized using bright field. However, the inventors were initially able to appreciate only a few some small, immobilized spots of rhodamine signal in the vessels in or immediately adjacent to the tumor (FIG. 13B-C). The high background in the Rhodamine channel (FIG. 13C) is the result of the high exposure time needed (300 ms) to capture a signal. At 30 minutes after the initial MB injection (in order to allow MB clearance from the circulation by the lungs), the inventors then introduced $4\times10^{11}$ NDs composed of DSPC, DSPE-PEG, DSPE-PEG-maleimide in a 90:8:2 molar ratio into the left retro-orbital sinus. NDs were conjugated with an anti-phosphatidylserine (PS) antibodies. While only a sparse number of MBs were observed pre-ND infusion in the rhodamine channel (FIG. 23C), more MB signal was observed (FIG. 23D) and immediately adjacent to the tumor, around 10 min post ND injection. The lower background is possibly due to reduction of the exposure time (250 ms). FIG. 23 shows a demonstration of MB targeting and inflation in vivo after intravenous NDs infusion. A) Dorsal skin flap as prepared for microscopy with sub-centimeter subcutaneous MC38 tumor. The nose cone and isoflurane anesthesia were temporarily removed for the purpose of taking this picture. B-C) Representative bright Field (B) and fluorescence microscopy images (C) of targeted MBs prior NDs injection. D) Representative fluorescence microscopy images of inflated MBs after 12 min post NDs injection. Scale bar is 100 μm.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference.

1. Wu Y, Unger E C, Mccreery T P, Sweitzer R H, Shen D, Wu G, Vielhauer M D. Binding and lysing of blood clots using MRX-408. Invest Radio/. 1998 December; 33(12): 880-5.
2. Lindner J R, Song J, Christiansen J, Klibanov A L, Xu F, Ley K. Ultrasound assessment of inflammation and renal tissue injury with microbubbles targeted to P-selectin. Circulation. 2001 Oct. 23; 104(17):2107-12.
3. Weller G E R, Lu E, Csikari M M, Klibanov A L, Fischer D, Wagner W R, Villanueva F S. Ultrasound Imaging of Acute Cardiac Transplant Rejection With Microbubbles Targeted to Intercellular Adhesion Molecule-1. Circulation 2003; 108:218-224.
4. Ellegala D B, Leong-Poi H, Carpenter J E, Klibanov A L, Kaul S, Shaffrey M E, Sklenar J, Lindner J R. Imaging Tumor Angiogenesis With Contrast Ultrasound and Microbubbles Targeted to Alpha-v Beta-3. Circulation 2003; 108:336-341.
5. Hall C S, Marsh J N, Scott M J, Gaffney P J, Wickline S A, Lanza G M. Time evolution of enhanced ultrasonic reflection using a fibrin-targeted nanoparticulate contrast agent. J Acoust Soc Am. 2000; 108(6):3049-57.
6. Lanza G M, Abendschein D R, Hall C S, Scott M J, Scherrer D E, Houseman A, Miller J G, Wickline S A. In vivo molecular imaging of stretch-induced tissue factor in carotid arteries with ligand-targeted nanoparticles. J Am Soc Echocardiogr. 2000 June; 13(6):608-14.
7. Mattrey R F, Steinbach G C: Ultrasound Contrast Agents: State of the Art. Invest Radio/. 1991; 26:S5-S11.
8. Ophir J, Parker K J. Contrast agents in diagnostic ultrasound [published erratum appears in Ultrasound Med Biol 1990; 16:209] Ultrasound Med Bio/ 1989; 15(4):319-33
9. Tiemann K, Becher H, Bimmel D, Schlief R, Nanda N C. Stimulated Acoustic Emission Nonbackscatter Contrast Effect of Microbubbles Seen with Harmonic Power Doppler Imaging. Echocardiography. 1997 January; 14(1):65-70
10. Klibanov A L, Rasche P T, Hughes M S, Wojdyla J K, Galen K P, Wible J H, Brandenburger G H. Detection of Individual Microbubbles of Ultrasound Contrast Agents Imaging of Free-Floating and Targeted Bubbles. Invest Radiol 2004; 39: 187-195
11. Hauff P, Reinhardt M, Briel A, Debus N, Schirner M. Molecular Targeting of Lymph Nodes with L-Selectin Ligand-specific US Contrast Agent: A Feasibility Study in Mice and Dogs. Radiology. 2004 in press [Epub ahead of print]
12. Jolesz F A, Hynynen K. Magnetic resonance image-guided focused ultrasound surgery. Cancer J. 2002; 8 (Suppl 1):S100-12.
13. Tempany C M, Stewart E A, McDannold N, Quade B J, Jolesz F A, Hynynen K. M R imaging-guided focused ultrasound surgery of uterine leiomyomas: a feasibility study. Radiology 2003; 226:897-905.
14. Oleson J R, Cetas T C, Corry P M. Hyperthermia by Magnetic Induction: Experimental and Theoretical Results for Coaxial Coil Pairs. Radiation Research 1983; 95:175-186
15. Reilly J P. Principles of Nerve and Heart Excitation by Time-Varying Magnetic Fields. Annual New York Academy of Science 1992; 649:96-117.
16. Jordan A, Scholz R, Maier-Hau K, Johannsen M, Wust P, Nadobny J, Schirra H, Schmidt H, Deger S, Loaning S, Lanksch W, Felix R. Presentation of a new magnetic field therapy system for the treatment of human solid tumours with magnetic fluid hyperthermia. J. Magn. Magn. Mater. 2001; 225:118-126.
17. Suzuki M, Shinkai M, Honda H, Kobayashi T. Anticancer effect and immune induction by hyperthermia of malignant melanoma using magnetite cationic liposomes. Melanoma Research 2003; 13:129-135.
18. Matsuoka F, Shinkai M, Honda H, Kubo T, Sugita T, Kobayashi T. Hyperthermia using magnetite cationic liposomes for hamster osteosarcoma. BioMagn Res Technol 2004; 2:3-8.
19. Shinkai M, Ueda K, Ohtsu S, Honda H, Kohri K, Kobayashi T. Effect of Functional Magnetic Particles on Radiofrequency Capacitive Heating: An in vivo Study. Jpn. J. Cancer Res 2002; 93:103-108.
20. Shinkai M, Le B, Honda H, Yoshikawa K, Shimizu K, Saga S, Wakabayashi T, Yoshida J, Kobayashi T. Targeting Hyperthermia for Renal Cell Carcinoma Using Human MN Antigen specific Magnetoliposomes. Jpn. J. Cancer Res 2001; 92: 1138-1146.
21. Moroz P, Jones S K. Gray B N. Magnetically mediated hyperthermia: current status and future directions. Int. J. Hyperthermia 2002; 18: 267-284.
22. Jordan A, Scholz R, Wust P, Fahling H, Krause J, Wlodarczyk W, Sander B, Vogl T, Felix R. Effects of magnetic fluid hyperthermia (MFH) on C3H mammary carcinoma in vivo. Int. J. Hyperthermia 1997; 13:587-605
23. Rosensweig R E. Heating magnetic fluid with alternating magnetic field. J. Magn. Magn. Mater. 2002; 252:370-374
24. Pankhurst Q A, Connolly J, Jones S K, Dobson J. Applications of Magnetic Nanoparticles in Biomedicine. Journal of Physics D: Applied Physics 2003; 36:R167-181
25. Giesecke T, Hynynen K. Ultrasound-mediated cavitation thresholds of liquid perfluorocarbon droplets in vitro. Ultrasound Med Biol. 2003; 29:1359-1365
26. Kripfgans O D, Fowlkes J B, Miller D L, Eldevik O P, Carson P L Acoustic droplet vaporization for therapeutic and diagnostic applications. Ultrasound Med Biol. 2000 September; 26(7): 1177-89.
27. Dayton P A, Allen J S, Ferrara K W. The magnitude of radiation force on ultrasound contrast agents. J. Acoust. Soc. Am 2002; 112: 2183-2192
28. Chomas J E, Dayton P A, May D J, Allen J S, Klibanov A L, Ferrara K W. Optical observation of contrast agent destruction. Appl. Phys. Lett. 2000; 77: 1056-1058.
29. Fink M, Montaldo G, Tanter M. Time-reversal acoustics in biomedical engineering. Annu Rev Biomed Eng. 2003; 5:465-97.
30. Mattrey R F, Long D M, Peck W W, Slutsky R A, Higgins C B: Perfluorooctyl bromide as a Blood Pool Contrast Agent for Liver, Spleen, and Vascular Imaging in Computed Tomography. J Comput Assist Tomogr. 1984; 8(4): 739-744.

Additional References

1. Mattrey R F. Perfluorooctylbromide: a new contrast agent for CT, sonography, and MR imaging. AJR Am J Roentgenol. 1989; 152(2):247-52. doi: 10.2214/ajr.152.2.247. PubMed PMID: 2643258.
2. Klibanov A L, Rasche P T, Hughes M S, Wojdyla J K, Galen K P, Wible J H, Jr., Brandenburger G H. Detection of individual microbubbles of an ultrasound contrast agent: fundamental and pulse inversion imaging. Acad Radiol. 2002; 9 Suppl 2:S279-81. PubMed PMID: 12188248.
3. Klibanov A L, Rasche P T, Hughes M S, Wojdyla J K, Galen K P, Wible J H, Brandenburger G H. Detection of individual microbubbles of ultrasound contrast agents— Imaging of free-floating and targeted bubbles. Invest Radiol. 2004; 39(3):187-95. doi: 10.1097/01.rli.0000115926.96796.75. PubMed PMID: WOS:000189320200008.
4. Cui W, Tavri S, Benchimol M J, Itani M, Olson E S, Zhang H, Decyk M, Ramirez R G, Barback C V, Kono Y, Mattrey R F. Neural progenitor cells labeling with microbubble contrast agent for ultrasound imaging in vivo. Biomaterials. 2013; 34(21):4926-35. doi: 10.1016/j.biomaterials.2013.03.020. PubMed PMID: 23578557; PMCID: PMC3742341.
5. Lindner J R, Song J, Christiansen J, Klibanov A L, Xu F, Ley K. Ultrasound assessment of inflammation and renal tissue injury with microbubbles targeted to P-selectin. Circulation. 2001; 104(17):2107-12. PubMed PMID: 11673354.
6. Leong-Poi H, Christiansen J, Klibanov A L, Kaul S, Lindner J R. Noninvasive assessment of angiogenesis by ultrasound and microbubbles targeted to alpha(v)-integrins. Circulation. 2003; 107(3):455-60. doi: 10.1161/01.Cir.0000044916.05919.8b. PubMed PMID: WOS:000180786100034.
7. Simberg D, Mattrey R. Targeting of perfluorocarbon microbubbles to selective populations of circulating blood cells. J Drug Target. 2009; 17(5):392-8. doi: 10.1080/10611860902902797. PubMed PMID: WOS:000268243000005.
8. Lux J, Vezeridis A M, Hoyt K, Adams S R, Armstrong A M, Sirsi S R, Mattrey R F. Thrombin-Activatable Microbubbles as Potential Ultrasound Contrast Agents for the Detection of Acute Thrombosis. ACS Appl Mater Interfaces. 2017; 9(43):37587-96. Epub 2017 Oct. 2011. doi: 10.1021/acsami.7b10592. PubMed PMID: 28994575; PMCID: PMC5691601.
9. Nakatsuka M A, Mattrey R F, Esener S C, Cha J N, Goodwin A P. Aptamer-crosslinked microbubbles: smart contrast agents for thrombin-activated ultrasound imaging. Adv Mater. 2012; 24(45):6010-6. Epub 2012 Sep. 2004. doi: 10.1002/adma.201201484. PubMed PMID: 22941789; PMCID: PMC3626403.
10. Mattrey R F, Steinbach G C. Ultrasound contrast agents. State of the art. Invest Radiol. 1991; 26 Suppl 1:S5-11; discussion S5. PubMed PMID: 1808149.
11. Behan M, O'Connell D, Mattrey R F, Carney D N. Perfluorooctylbromide as a contrast agent for CT and sonography: preliminary clinical results. AJR Am J Roentgenol. 1993; 160(2):399-405. doi: 10.2214/ajr.160.2.8424361. PubMed PMID: 8424361.
12. Kripfgans O D, Fowlkes J B, Miller D L, Eldevik O P, Carson P L. Acoustic droplet vaporization for therapeutic and diagnostic applications. Ultrasound Med Biol. 2000; 26(7):1177-89. PubMed PMID: 11053753.
13. Schutt E G, Klein D H, Mattrey R M, Riess J G. Injectable microbubbles as contrast agents for diagnostic ultrasound imaging: the key role of perfluorochemicals. Angew Chem Int Ed Engl. 2003; 42(28):3218-35. doi: 10.1002/anie.200200550. PubMed PMID: 12876730.
14. Beppu S, Matsuda H, Shishido T, Matsumura M, Miyatake K. Prolonged myocardial contrast echocardiography via peripheral venous administration of QW3600 injection (EchoGen): its efficacy and side effects. J Am Soc Echocardiogr. 1997; 10(1):11-24. PubMed PMID: 9046489.
15. Grayburn P A, Erickson J M, Escobar J, Womack L, Velasco C E. Peripheral intravenous myocardial contrast echocardiography using a 2% dodecafluoropentane emulsion: identification of myocardial risk area and infarct size in the canine model of ischemia. J Am Coll Cardiol. 1995; 26(5):1340-7. doi: 10.1016/0735-1097(95)00306-1. PubMed PMID: 7594052.
16. Robbin M L, Eisenfeld A J. Perflenapent emulsion: a US contrast agent for diagnostic radiology—multicenter, double-blind comparison with a placebo. EchoGen Contrast Ultrasound Study Group. Radiology. 1998; 207(3): 717-22. doi: 10.1148/radiology.207.3.9609895. PubMed PMID: 9609895.
17. Ho Y-J, Yeh C-K. Theranostic performance of acoustic nanodroplet vaporization-generated bubbles in tumor intertissue. Theranostics. 2017; 7(6):1477-88. doi: doi: 10.7150/thno.19099
18. Chen C C, Sheeran P S, Wu S Y, Olumolade O O, Dayton P A, Konofagou E E. Targeted drug delivery with focused ultrasound-induced blood-brain barrier opening using acoustically-activated nanodroplets. J Control Release. 2013; 172(3):795-804. doi: 10.1016/j.jconrel.2013.09.025. PubMed PMID: 24096019; PMCID: PMC3866692.
19. Wu S Y, Fix S M, Arena C B, Chen C C, Zheng W, Olumolade O O, Papadopoulou V, Novell A, Dayton P A, Konofagou E E. Focused ultrasound-facilitated brain drug delivery using optimized nanodroplets: vaporization efficiency dictates large molecular delivery. Phys Med Biol. 2018; 63(3):035002. doi: 10.1088/1361-6560/aaa30d. PubMed PMID: 29260735; PMCID: PMC5823501.
20. Moyer L C, Timbie K F, Sheeran P S, Price R J, Miller G W, Dayton P A. High-intensity focused ultrasound ablation enhancement in vivo via phase-shift nanodroplets compared to microbubbles. J Ther Ultrasound. 2015; 3:7. doi: 10.1186/s40349-015-0029-4. PubMed PMID: 26045964; PMCID: PMC4455327.
21. Ferretti S, Allegrini P R, Becquet M M, McSheehy P M J. Tumor Interstitial Fluid Pressure as an Early-Response Marker for Anticancer Therapeutics. Neoplasia. 2009; 11(9):874-81. doi: 10.1593/neo.09554. PubMed PMID: WOS:000270038200006.
22. Samuel S, Duprey A, Fabiilli M L, Bull J L, Fowlkes J B. In vivo microscopy of targeted vessel occlusion employing acoustic droplet vaporization. Microcirculation. 2012; 19(6):501-9. doi: 10.1111/j.1549-8719.2012.00176.x. PubMed PMID: 22404846; PMCID: PMC3414215.
23. Sheeran P S, Wong V P, Luois S, McFarland R J, Ross W D, Feingold S, Matsunaga T O, Dayton P A. Decafluorobutane as a phase-change contrast agent for low-energy extravascular ultrasonic imaging. Ultrasound Med Biol. 2011; 37(9):1518-30. doi: 10.1016/j.ultrasmedbio.2011.05.021. PubMed PMID: 21775049; PMCID: PMC4450864.
24. Lo A H, Kripfgans O D, Carson P L, Rothman E D, Fowlkes J B. Acoustic droplet vaporization threshold: effects of pulse duration and contrast agent. IEEE Trans Ultrason Ferroelectr Freq Control. 2007; 54(5):933-46. PubMed PMID: 17523558.
25. Hutter J C, Luu H M, Mehlhaff P M, Killam A L, Dittrich H C. Physiologically based pharmacokinetic model for fluorocarbon elimination after the administration of an octafluoropropane-albumin microsphere sonographic contrast agent. J Ultrasound Med. 1999; 18(1):1-11. PubMed PMID: 9952073.
26. Okada M, Albrecht T, Blomley M J, Heckemann R A, Cosgrove D O, Wolf K J. Heterogeneous delayed enhancement of the liver after ultrasound contrast agent injection—a normal variant. Ultrasound Med Biol. 2002; 28(8):1089-92. PubMed PMID: 12217445.
27. Caruso G, Martegani A, Aiani L, Borghi C, Verderame F, Campisi A, Salvaggio G, Lagalla R, Cardinale A E. Heterogeneous delayed enhancement of hepatic parenchyma after intravenous infusion of sonographic contrast agent: a new hypothesis. Radiol Med. 2007; 112(1):56-63. doi: 10.1007/s11547-007-0120-1. PubMed PMID: 17310291.
28. Al-Husein B, Abdalla M, Trepte M, Deremer D L, Somanath P R. Antiangiogenic therapy for cancer: an update. Pharmacotherapy. 2012; 32(12):1095-111. doi: 10.1002/phar.1147. PubMed PMID: 23208836; PMCID: PMC3555403.
29. de Gracia Lux C, Vezeridis A M, Lux J, Armstrong A M, Sirsi S R, Hoyt K, Mattrey R F. Novel method for the formation of monodisperse superheated perfluorocarbon nanodroplets as activatable ultrasound contrast agents. RSC Adv. 2017; 7(77):48561-8. doi: 10.1039/C7RA08971F. PubMed PMID: 29430294; PMCID: PMC5801773.
30. Riess J G. Understanding the fundamentals of perfluorocarbons and perfluorocarbon emulsions relevant to in vivo oxygen delivery. Artif Cells Blood Substit Immobil Biotechnol. 2005; 33(1):47-63. Epub 2005 Mar. 17. PubMed PMID: 15768565.
31. Miyoshi T, Kato S. Detailed Analysis of the Surface Area and Elasticity in the Saturated 1,2-Diacylphosphatidylcholine/Cholesterol Binary Monolayer System. Langmuir. 2015; 31(33):9086-96. Epub 2015 Aug. 11. doi: 10.1021/acs.langmuir.5b01775. PubMed PMID: 26255826.
32. Borden M A, Longo M L. Dissolution behavior of lipid monolayer-coated, air-filled microbubbles: Effect of lipid hydrophobic chain length. Langmuir. 2002; 18(24):9225-33. doi: 10.1021/la026082h. PubMed PMID: WOS: 000179428400018.

33. Mountford P A, Thomas A N, Borden M A. Thermal activation of superheated lipid-coated perfluorocarbon drops. Langmuir. 2015; 31(16):4627-34. Epub 2015 Apr. 9. doi: 10.1021/acs.langmuir.5b00399. PubMed PMID: 25853278.
34. Kooiman K, Kokhuis T J A, van Rooij T, Skachkov I, Nigg A, Bosch J G, van der Steen A F W, van Cappellen W A, de Jong N. DSPC or DPPC as main shell component influences ligand distribution and binding area of lipid-coated targeted microbubbles. Eur J Lipid Sci Tech. 2014; 116(9):1217-27. doi: 10.1002/ejlt.201300434. PubMed PMID: WOS:000343000600014.
35. Baskin J M, Prescher J A, Laughlin S T, Agard N J, Chang P V, Miller I A, Lo A, Codelli J A, Bertozzi C R. Copper-free click chemistry for dynamic in vivo imaging. P Natl Acad Sci USA. 2007; 104(43):16793-7. doi: DOI 10.1073/pnas.0707090104. PubMed PMID: WOS:000250487600015.
36. Chang P V, Prescher J A, Sletten E M, Baskin J M, Miller I A, Agard N J, Lo A, Bertozzi C R. Copper-free click chemistry in living animals. P Natl Acad Sci USA. 2010; 107(5):1821-6. doi: 10.1073/pnas.0911116107. PubMed PMID: WOS:000274296300006.
37. Brudno Y, Desai R M, Kwee B J, Joshi N S, Aizenberg M, Mooney D J. In Vivo Targeting through Click Chemistry. Chemmedchem. 2015; 10(4):617-20. doi: 10.1002/cmdc.201402527. PubMed PMID: WOS:000351773300005.
38. Whitehead S A, McNitt C D, Mattern-Schain S I, Carr A J, Alam S, Popik V V, Best M D. Artificial Membrane Fusion Triggered by Strain-Promoted Alkyne—Azide Cycloaddition. Bioconjugate Chemistry. 2017; 28(4):923-32. doi: 10.1021/acs.bioconjchem.6b00578.
39. Righi M, Puleo G L, Tonazzini I, Giudetti G, Cecchini M, Micera S. Peptide-based coatings for flexible implantable neural interfaces. Sci Rep. 2018; 8(1):502. doi: 10.1038/s41598-017-17877-y. PubMed PMID: 29323135; PMCID: PMC5765121.
Simberg D, Mattrey R F. Targeting of perfluorocarbon microbubbles to selective populations of circulating blood cells. Journal of drug targeting; 2009, 17:392-8.
PCT Publication No. WO2009052057
U.S. Pat. Publication No. 20170176305
U.S. Pat. Publication No. 20160167061

What is claimed:

1. A method of increasing bubble size, the method comprising:
    providing bubbles to a region of interest, wherein the bubbles comprise a perfluorocarbon gas and have an average bubble diameter between 200 nm and 10 µm;
    providing nanodroplets comprising a perfluorocarbon liquid to the region of interest,
    wherein the average diameter of the bubbles that are in the region of interest is increased by the nanodroplets.
2. The method of claim 1, wherein the bubbles and nanodroplets are provided sequentially to the region of interest.
3. The method of claim 2, wherein the bubbles are provided prior to the nanodroplets.
4. The method of claim 2, wherein the nanodroplets are provided prior to the bubbles.
5. The method of claim 2, wherein the bubbles comprise a perfluorocarbon gas having a 4 carbon chain.
6. The method of claim 2, wherein the bubbles comprise a perfluorocarbon gas having a 5 carbon chain.
7. The method of claim 2, wherein the nanodroplets comprise a perfluorocarbon liquid having a 4 carbon chain.
8. The method of claim 2, wherein the nanodroplets comprise a perfluorocarbon liquid having a 5 carbon chain.
9. The method of claim 2, wherein the bubbles and nanodroplets are provided in a ratio of at least about 10 nanodroplets per bubble.
10. The method of claim 9, wherein the bubbles and nanodroplets are provided in a ratio of at least about 100 nanodroplets per bubble.
11. The method of claim 2, wherein the average volume of the bubbles is increased by at least two orders of magnitude.
12. The method of claim 11, wherein the average volume of the bubbles in increased by at least six orders of magnitude.
13. The method of claim 2, wherein the nanodroplets and bubbles are functionalized to bind each other.
14. A method of inflating bubbles within the body of a subject, the method comprising:
    administering the bubbles to the subject, wherein the bubbles comprise a perfluorocarbon gas and have an average bubble diameter between 200 nm and 10 µm; and
    administering nanodroplets comprising a perfluorocarbon liquid to the subject;
    wherein the bubbles and nanodroplets are administered sequentially to the subject and the average diameter of the bubbles is increased by the nanodroplets.
15. The method of claim 14, wherein the bubbles and/or the nanodroplets are functionalized to target an intravascular site.
16. The method of claim 14, wherein the bubbles and/or the nanodroplets are functionalized to target an extravascular site.
17. The method of claim 14, wherein the bubbles and/or the nanodroplets are functionalized to bind a cell surface receptor of interest.
18. The method of claim 14, wherein the bubbles and/or the nanodroplets comprise an antibody for targeting a specific cell type or tissue type.
19. The method of claim 14, wherein the bubbles and/or the nanodroplets are functionalized to target phosphatidylserine.
20. The method of claim 14, further comprising imaging the inflated bubbles with ultrasound, wherein the increase in the average diameter of the inflated bubbles provides at least a 4-fold enhancement of the ultrasound signal.

* * * * *